United States Patent
Chang et al.

(10) Patent No.: US 10,586,327 B2
(45) Date of Patent: Mar. 10, 2020

(54) METHOD AND APPARATUS FOR DETECTING CELL REPROGRAMMING

(71) Applicants: Chung Yuan Christian University, Taoyuan (TW); RIKEN, Saitama (JP)

(72) Inventors: Yuan-Hsiang Chang, Taoyuan (TW); Hideo Yokota, Saitama (JP); Kuniya Abe, Ibaraki (JP); Ming-Dar Tsai, Taoyuan (TW)

(73) Assignees: CHUNG YUAN CHRISTIAN UNIVERSITY, Taoyuan (TW); RIKEN, Saitama (JP)

(\*) Notice: Subject to any disclaimer, the term of this patent is extended or adjusted under 35 U.S.C. 154(b) by 68 days.

(21) Appl. No.: 15/894,945

(22) Filed: Feb. 13, 2018

(65) Prior Publication Data
US 2018/0232879 A1    Aug. 16, 2018

(30) Foreign Application Priority Data
Feb. 15, 2017 (JP) ................. 2017-026477

(51) Int. Cl.
| | | |
|---|---|---|
| G06K 9/00 | (2006.01) | |
| G06T 7/00 | (2017.01) | |
| G02B 21/16 | (2006.01) | |
| G02B 21/36 | (2006.01) | |
| G01N 33/58 | (2006.01) | |
| G01N 33/50 | (2006.01) | |
| G01N 21/64 | (2006.01) | |
| G06T 7/90 | (2017.01) | |

(52) U.S. Cl.
CPC ....... *G06T 7/0012* (2013.01); *G01N 21/6428* (2013.01); *G01N 21/6486* (2013.01); *G01N 33/5005* (2013.01); *G01N 33/582* (2013.01); *G02B 21/16* (2013.01); *G02B 21/367* (2013.01); *G06K 9/00147* (2013.01); *G06T 7/90* (2017.01); *G01N 2021/6441* (2013.01); *G06T 2207/10024* (2013.01); *G06T 2207/10056* (2013.01); *G06T 2207/10064* (2013.01); *G06T 2207/20081* (2013.01); *G06T 2207/20084* (2013.01); *G06T 2207/30024* (2013.01)

(58) Field of Classification Search
CPC ............................................. G01N 2021/6441
See application file for complete search history.

(56) References Cited

U.S. PATENT DOCUMENTS

| | | | |
|---|---|---|---|
| 2003/0016846 A1\* | 1/2003 | Chen ............... | G06K 9/00268 382/117 |
| 2009/0081775 A1\* | 3/2009 | Hodneland ........ | G01N 15/1468 435/317.1 |

(Continued)

OTHER PUBLICATIONS

Chang et al, "Detection and Localization of Mouse Induced Pluripotent Stem Cell Formation using Time-Lapse Fluorescence Microscopy Images", IEEE.

(Continued)

*Primary Examiner* — Oneal R Mistry

(57) ABSTRACT

Disclosed herein are methods for identifying cells undergoing reprogramming and reprogrammed cells from a fluorescence microscopic image of one or more cells. According to some embodiments, the method includes an image processing step, a cell detection step, and, optionally, a clustering step.

16 Claims, 14 Drawing Sheets
(8 of 14 Drawing Sheet(s) Filed in Color)

(56) References Cited

U.S. PATENT DOCUMENTS

| | | | |
|---|---|---|---|
| 2009/0324051 A1* | 12/2009 | Hoyt | G01N 1/30 |
| | | | 382/133 |
| 2017/0109563 A1* | 4/2017 | Kilgore | G06K 9/00087 |
| 2017/0309021 A1* | 10/2017 | Barnes | G06T 7/0012 |
| 2018/0114317 A1* | 4/2018 | Song | G06K 9/6265 |

OTHER PUBLICATIONS

Chang et al, "Human Induced Pluripotent Stem Cell Region Recognition in Microscopy Images Using Convolutional Neural Networks", IEEE.

* cited by examiner

| IWP-2 Colony 1 | | | |
|---|---|---|---|
| D | Original image | Class 4+5 | Class 6 | Inversed Class 1 |
| 4 | | | | |
| 7 | | | | |
| 8 | | | | |
| 9 | | | | |
| 10 | | | | |
| 11 | | | | |

FIG. 11A

| Control Colony 2 | | | |
|---|---|---|---|
| D | Original image | Class 4+5 | Class 6 | Inversed Class 1 |
| 4 | | | | |
| 7 | | | | |
| 8 | | | | |
| 9 | | | | |
| 10 | | | | |
| 11 | | | | |

FIG. 12A

METHOD AND APPARATUS FOR DETECTING CELL REPROGRAMMING

STATEMENT REGARDING PRIOR DISCLOSURES BY THE INVENTOR OR A JOINT INVENTOR UNDER 37 C.F.R. 1.77(B)(6)

Part of the subject matter of the invention described in the present application was published by the inventors, Yuan-Hsiang Chang, Hideo Yokota, Kuniya Abe, and Ming-Dar Tsai in an article titled "Detection and Localization of Mouse Induced Pluripotent Stem Cell Formation using Time-Lapse Fluorescence Microscopy Images;" this article was disclosed during the 2016 38th Annual International Conference of the IEEE Engineering in Medicine and Biology Society (EMBC) held between 16-20 Aug. 2016 and published online by IEEE Xplore on 18 Oct. 2016. Part of the subject matter of the invention described in the present application was published by the inventors, Yuan-Hsiang Chang, Hideo Yokota, Kuniya Abe, and Ming-Dar Tsai in an article titled "Human induced pluripotent stem cell region recognition in microscopy images using Convolutional Neural Networks;" this article was disclosed during the 2017 39th Annual International Conference of the IEEE Engineering in Medicine and Biology Society (EMBC) held between 11-15 Jul. 2017 and published online by IEEE Xplore on 14 Sep. 2017. Therefore, these publications or disclosures were made by and/or originated from all member of the inventive entity of the present invention less than one year before the filing date of the present application. A copy of each article is provided in a concurrently filed Information Disclosure Statement pursuant to the guidance of 78 Fed. Reg. 11076 (Feb. 14, 2013).

CROSS REFERENCE TO RELATED APPLICATION

The disclosure of Japanese Patent Application No. 2017-026477 filed on Feb. 15, 2017, including the specification, claims, drawings and abstract, is incorporated herein by reference in its entirety.

BACKGROUND OF THE INVENTION

1. Field of the Invention

The present disclosure relates to the identification of cell reprogramming process; more particularly, to methods and apparatuses for detecting cells undergoing reprogramming or reprogrammed cells.

2. Description of Related Art

Induced pluripotent stem (iPS) cells are pluripotent cells generated from differentiated cells. Cells, such as fibroblasts, are induced into a pluripotent state by introducing genes encoding specific transcription factors into cells using viral vectors, adenovirus, plasmids, and naked DNA. iPS cells present an ideal source for patient-specific cell-based regenerative medicine because potential issues of allogeneic immune rejection can be avoided.

iPS cells have been established from various mammalian cells including human cells and successfully induced into differentiated cells to make tissues or organ-like structures in vitro. Currently, clinical studies and trials, such as iPS cell-derived retinal pigment epithelium, have been initiated. To foster practical medical uses of iPS cells, large-scale expansion of iPS cells and methods for correcting possible mutations occurring during the iPS formation are urgently pursed.

However, when using viral vectors, the efficiency for iPS cell induction is generally low, ranging from 0.001-0.1%. Accordingly, only a small subset of cells becomes the iPS cells within a vast population non-iPS cells. Therefore, it is a burdensome task to identify and trace cells undergoing reprogramming. Further, a detailed "route map" from differentiated cells to iPS cells has not been obtained thus far.

One approach to trace the reprogramming process is to use a fluorescent reporter gene driven by the promoter of pluripotency genes such as Oct4. Then, time-lapse fluorescent microscopic analysis is used to capture a series of images of the reprogramming cells, which provides an overview of the reprogramming process. Nonetheless, a manual analysis of the time-lapse images is a labor-intensive, time-consuming, and often inaccurate.

In view of the foregoing, there exists a need in the related art to provide a method capable of automatically detecting the cells undergoing the reprogramming process or cells that have been reprogrammed.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In one aspect, the present disclosure is directed to a method that automatically identifies cells undergoing reprogramming and reprogrammed cells from a fluorescence microscopic image of one or more cells. In some embodiments, the method automatically processes a series of fluorescence microscopic images and detects the beginning of the reprogramming process, as well as the location where the reprogramming process takes place.

According to some embodiments of the present disclosure, the method comprising the following steps: (a) applying grayscale conversion and unsharp masking to the fluorescence microscopic image to obtain an enhanced image; (b) convert the enhanced image to a binary image; (c) identifying a cell-like ellipse boundary for cells in the binary image, wherein each cell-like ellipse boundary represent an isolated cells or a group of cells; and (d) labeling each isolated cell or group of cells with a random color to obtain a plurality of colored components, wherein each color component represents one or more cells undergoing reprogramming or one or more reprogrammed cells.

In some optional embodiments, the unsharp masking in the step (a) is performed by applying an unsharp mask according to equation 1:

$$f_s(x,y) = |f(x,y) - f(x,y) * G_\sigma| \qquad \text{(equation 1)},$$

where the $f_s(x,y)$ is the enhanced image, x and y are the image coordinates, * represents the image convolution, and $G_\sigma$ is the Gaussian filter with the standard deviation $\sigma$ and the filter size of $2\sigma+1$. In some embodiments, the filter size is the cell diameter.

According to some embodiments, the step (b) is performed according to equation 2:

$$g(x, y) = \begin{cases} 1 & f_s(x, y) \geq T \\ 0 & \text{otherwise} \end{cases} \quad \text{(equation 2)}$$

where T is the threshold for the fluorescence microscopy image. For example, the threshold is 3 in some embodiments.

In some optional embodiments, the method further comprises the step of, (e) evaluating the smoothness of each pixel of the colored components in relative to a local area of the pixel. Specifically, the step (e) is performed by (e-1) determining the magnitude of image gradients M(x,y) of each pixel according to equation 3:

$$M(x,y) = \sqrt{G_x^2 + G_y^2} \cdot \quad \text{(equation 3)},$$

where $G_x = \partial f/\partial x$ and $G_y = \partial f/\partial y$, Gx and Gy respectively represent the image gradients in x and y directions; and (e-2) determining the smoothness σ (x,y) of each pixel according to equation 4:

$$\sigma(x, y) = \frac{1}{N-1} \sum_x \sum_y (M(x, y) - \mu)^2, \quad \text{(equation 4)}$$

where N is the total number of pixels and μ is the mean pixel value in the local area. Moreover, the method further comprises the step of, (f) determining the presence of a vague region R that satisfies the criterion of equation 5:

$$R = \{(x,y): \sigma(x,y) \geq T\} \quad \text{(equation 5)}.$$

In some embodiments, the vague region represents a cell cluster.

According to optional embodiments of the present disclosure, the method comprises performing steps (a) to (f) to a series of fluorescence microscopic images of said one or more cells to identify the beginning of the cell reprogramming.

In another aspect, the present disclosure is directed to a tangible computer-readable storage medium encoded with computer-readable instructions (a computer program or software) that when executed by a programmable device (a processor or a computer) cause the programmable device to perform the present methods for identifying cells undergoing reprogramming and reprogrammed cells from a fluorescence microscopic image of one or more cells. All or various embodiments of the method according to the invention that are described herein can be executed by these encoded instructions when run in the programmable device.

In yet another aspect, the present invention is directed to a system for identifying cells undergoing reprogramming and reprogrammed cells from a fluorescence microscopic image of one or more cells.

According to certain embodiments, the system comprises, an apparatus configured to obtain a fluorescence microscopic image of one or more cells and a control unit that comprises a processor and a memory for storing a plurality of instructions which, when executed by the processor, causing the processor to perform the present method. All or various embodiments of the method according to the invention that are described herein can be executed by the processor.

In another aspect, the present disclosure is directed to a method that automatically identifies and tracks cells undergoing reprogramming and reprogrammed cells from a fluorescence microscopic image of one or more cells. In some embodiments, the method uses a deep learning framework to automatically processes a series of fluorescence microscopic images and detects the beginning of the reprogramming process, as well as the location where the reprogramming process takes place.

According to some embodiments of the present disclosure, the method comprises the steps of, (a) for every pixel of the fluorescence microscopic image, capturing an image of region of interest (ROI) of the pixel; (b) applying a trained convolutional neural network (CNN) model to the ROI to calculate the respective probabilities of the pixel belonging to any of a plurality of classes, wherein each of the plurality classes indicate a cell clustering pattern of the ROI; and (c) obtaining a plurality of probability maps that respectively indicate the probabilities of the plurality of classes at every pixel of the fluorescence microscopic image.

According to optional embodiments of the present disclosure, the method further comprises the step of (d) converting the fluorescence microscopic image into a gray-level image according to the plurality of probability maps. Still optionally, the method further comprises the step of (e) determining the conditions of reprogramming gray-level image.

According to certain optional embodiments, the method further comprises the following steps to established the CNN model: (1) selecting a region of a training image as a template image; (2) manually classifying the template image as belonging to one of the plurality of classes; (3) producing a training set comprising a plurality of template images from a plurality of training images by repeating steps (1) and (2); (4) using the plurality of template images of the training set as inputs to train an CNN architecture to obtain the trained CNN model.

According to various embodiments of the present disclosure, the pixel size of the ROI is at least 256 by 256 pixels. Further, in some embodiments, the pixel size of the template image is the same as the pixel size of the ROI.

In optional embodiments, the plurality of template images are divided into a first set of template images and a second set of template images, and the method further comprises the following steps to train the CNN model: using the first set of template images to calculate a plurality of parameters of the CNN model; using the second set of template images to calculate a plurality of error vectors of the plurality of parameters; and using the error vectors to re-calculate the parameters. For example, in some cases, a plurality of optimized parameters for the CNN model is obtained after 10,000 iterations.

In another aspect, the present disclosure is directed to a tangible computer-readable storage medium encoded with computer-readable instructions (a computer program or software) that when executed by a programmable device (a processor or a computer) cause the programmable device to perform the present methods for identifying and tracking cells undergoing reprogramming and reprogrammed cells from a fluorescence microscopic image of one or more cells. All or various embodiments of the method according to the invention that are described herein can be executed by these encoded instructions when run in the programmable device.

In yet another aspect, the present invention is directed to a system for identifying and tracking cells undergoing reprogramming and reprogrammed cells from a fluorescence microscopic image of one or more cells.

According to certain embodiments, the system comprises, an apparatus configured to obtain a fluorescence microscopic image of one or more cells and a control unit that comprises a processor and a memory for storing a plurality of instructions which, when executed by the processor, causing the processor to perform the present method. All or various embodiments of the method according to the invention that are described herein can be executed by the processor.

Many of the attendant features and advantages of the present disclosure will becomes better understood with reference to the following detailed description considered in connection with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present description will be better understood from the following detailed description read in light of the accompanying drawings, where:

FIG. 11A shows representative images of IWP-2 colony 1 cell cultures taken at specified days according to Embodiment 5, as well as the probability maps derived from the original images, whereas

FIG. 12A shows representative images of Control colony 2 cell cultures taken at specified days according to Embodiment 5, as well as the probability maps derived from the original images, whereas

DESCRIPTION

Figure 1:
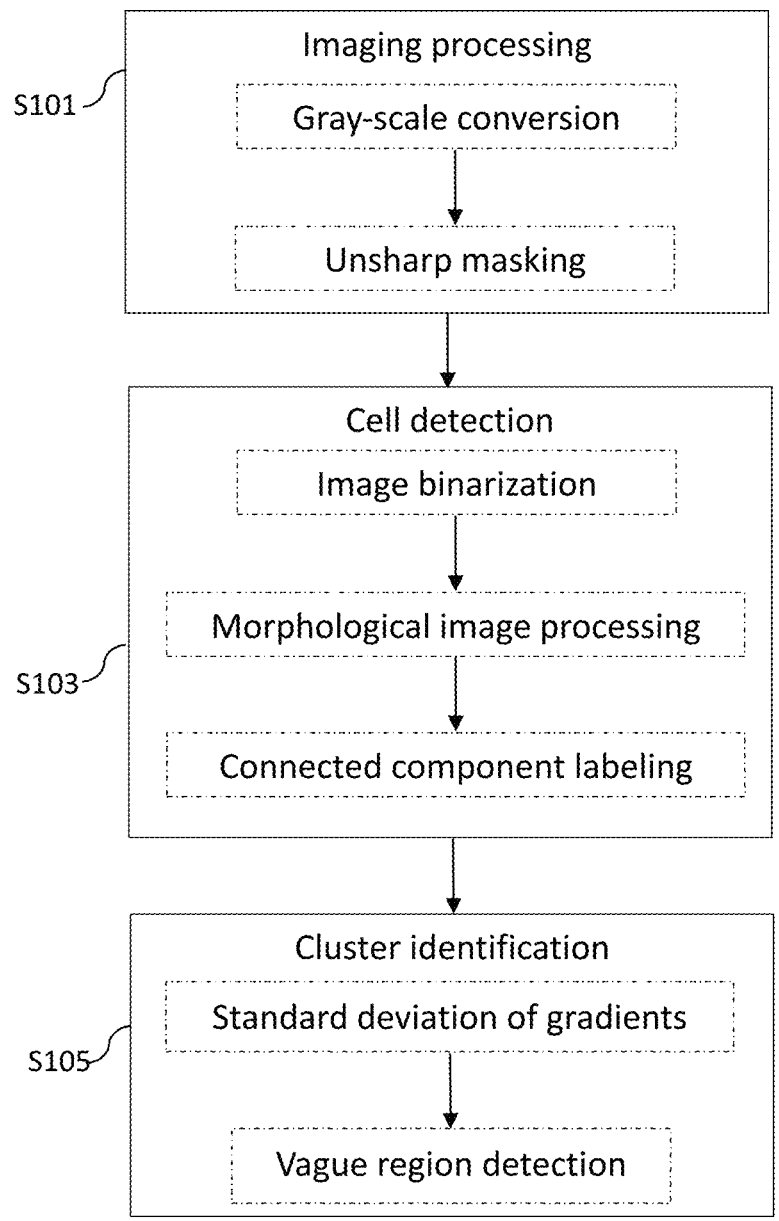
FIG. 1 is a flow diagram according to Embodiment 1 of the present disclosure; the flow diagram illustrates steps for performing the methods for identifying cells undergoing reprogramming and reprogrammed cells from a fluorescence microscopic image of one or more cells according to embodiments of the present disclosure.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art.

Unless otherwise required by context, it will be understood that singular terms shall include plural forms of the same and plural terms shall include the singular. Also, as used herein and in the claims, the terms "at least one" and "one or more" have the same meaning and include one, two, three, or more. Furthermore, the phrases "at least one of A, B, and C", "at least one of A, B, or C" and "at least one of A, B and/or C," as use throughout this specification and the appended claims, are intended to cover A alone, B alone, C alone, A and B together, B and C together, A and C together, as well as A, B, and C together.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

As used herein, the term "pluripotent" refers to a cell with the capacity, under different conditions, to differentiate to cell types characteristic of all three germ cell layers, i.e., endoderm (e.g., gut tissue), mesoderm (including blood, muscle, and vessels), and ectoderm (such as skin and nerve). Accordingly, the terms "pluripotency" or a "pluripotent state" as used herein refer to the developmental potential of a cell that provides the ability for the cell to differentiate into all three embryonic germ layers.

Throughout the present disclosure, the term, "induced pluripotent stem cells" or iPS cells, means that the stem cells are produced from differentiated adult cells that have been induced or changed (i.e., "reprogrammed") into cells capable of differentiating into tissues of all three germ or dermal layers.

The term "reprogramming" as used herein refers to the process of altering the differentiated state of a differentiated adult cell to a pluripotent phenotype. In other words, reprogramming refers to a process of driving a cell to a state with higher developmental potential, i.e., backwards to a less differentiated state. In some embodiments of the aspects described herein, reprogramming encompasses a complete or partial reversion of the differentiation state, i.e., an increase in the developmental potential of a cell, to that of a cell having a pluripotent state. Therefore, in some cases, the reprogramming of the present invention provides at least one dedifferentiated and/or rejuvenated cell, in particular provides a cell having the characteristic of a multi-potent, in particular pluripotent stem cell. The resulting cells are referred to herein as "reprogrammed cells."

Fluorescence imaging of live cells is a powerful tool for the study of dynamic cellular processes and events, such as embryogenesis and cell differentiation. With the advancement of the imaging technology, fluorescence imaging is capable of yielding high spatial and temporal resolution.

Embodiment 1

In view of the foregoing, the first aspect of the present disclosure is directed to a method for identifying cells undergoing reprogramming and reprogrammed cells from a fluorescence microscopic image of one or more cells.

FIG. 1 is a flow chart illustrating a method 100 according to embodiments of the present disclosure. According to FIG. 1, a fluorescence microscopic image is first subjected to an imaging processing step S101.

Specifically, the imaging processing step S101 comprises a grayscale conversion step, followed by an unsharp masking step, which are designed to remove the noise, thereby improving the signal-to-noise ratio of the fluorescence microscopy image.

For the unsharp masking step, an unsharp masking is applied to the grayscale-converted fluorescence microscopy image f(x,y) to obtain an enhanced image fs(x,y) according to equation 1:

$$f_s(x,y) | f(x,y) - f(x,y) * G_\sigma | \quad \text{(equation 1)},$$

where the $f_s(x,y)$ is the enhanced image, x and y are the image coordinates, * represents the image convolution, and $G_\sigma$ is the Gaussian filter with the standard deviation σ and the filter size of 2σ+1. In some optional embodiments, the filter size is selected as the cell diameter (e.g., about 20 μm).

Then, the enhanced image from the imaging processing step S101 is subjected to a cell detection step S103. This phase aims to detect every isolated cell or cells. First, in an image binarization step, the enhanced image fs(x,y) is converted to a binary image g(x,y) according to equation 2:

$$g(x, y) = \begin{cases} 1 & f_s(x, y) \geq T \\ 0 & \text{otherwise} \end{cases}, \quad \text{(equation 2)}$$

where T is the threshold for the fluorescence microscopy image. In some optional embodiments, T is the threshold with the value of 3 for the fluorescence microscopy images.

Still in the cell detection step S103, the binary image is subjected to a morphological image processing step, in which the contours fluorescent cells (reprogramming and reprogrammed iPS cells) are segmented. For example, a morphological closing technique (i.e., morphological dilation followed by erosion) is used in some embodiments to yield the cell-like ellipse boundary in which each cell-like ellipse boundary represents an isolated cell or a group of cells.

The final step of the cell detection step S103 is a connected component labeling step in which each isolated cell or group of cells (that is, the area confined by each cell-like ellipse boundary) is labeled with a random color to obtain a plurality of colored components, wherein each color component represents one or more cells undergoing reprogramming or one or more reprogrammed cells. As could be appreciated, in this step, any two or more of adjacent isolated cell or adjacent cell groups are preferably labeled with different colors. Further, judging from the scale of the fluorescence microscopic image, it is feasible to ascertain the pixel size of a single, isolated cell in the image, and this information can be used to determine whether a color component represents a single, isolated fluorescent cell, or a group of fluorescent cells. For example, in the cases where the width of each pixel is about 1 μm, an isolated detected fluorescent area is considered as consisting of multiple fluorescent cells if the area's pixel number along either x or y direction is over 20 pixels (about 20 μm).

As could be appreciated, after the connected component labeling step, one or more fluorescent cells or groups of fluorescent cells are identified, and hence, the method 100 may stop once the cell detection step S103 is accomplished, according to some embodiments of the present disclosure.

In optional embodiments, the method 100 further comprises a cluster identification step S105. This phase aims to identify beginning of the iPS cell formation. At the beginning of the iPS cell formation, the reprogramming cells often stack with one another. Therefore, searching for the presence of the cluster in the fluorescence microscopy image helps identify the beginning of the reprogramming process. This is particular useful in embodiments where two or more of fluorescence microscopic images are processed sequentially, so that the present method 100 can be used to automatically identify when and where does iPS cell formation take place.

Specifically, the cluster identification step S105 comprises a step for determining the standard deviation of gradients and a vague region detection step.

The standard deviation of gradients is first determined to quantitatively evaluate the vagueness for each pixel in a local area. First, the magnitude of image gradients M(x,y) are computed according to equation 3:

$$M(x,y) = \sqrt{G_x^2 + G_y^2}, \quad \text{(equation 3)},$$

where $G_x = \partial f/\partial x$ and $G_y = \partial f/\partial y$, Gx and Gy respectively represent the image gradients in x and y directions. Then, the vagueness (smoothness) of each pixel σ(x,y) is defined as the standard deviation of image gradients in a local area according to equation 4:

$$\sigma(x, y) = \frac{1}{N-1} \sum_x \sum_y (M(x, y) - \mu)^2, \quad \text{(equation 4)}$$

where N is the total number of pixels and μ is the mean pixel value in the local area. For example, in some embodiments, the local area was selected as 11 by 11 pixels (approximately, 10 μm×10 μm).

Next, in the vague region detection step, the vague region that is likely to represent the possible reprogrammed cell cluster is automatically detected. In the present disclosure, a vague region is defined as a region R that satisfies the criterion of equation 5:

$$R=\{(x,y):\sigma(x,y)\geq T\} \quad \text{(equation 5)}.$$

where T is a threshold. As could be appreciated, each vague region represents a cell cluster.

According to certain embodiments of the present disclosure, the present method can be implemented as a computer product that is developed using the Open Source Computer Vision (OpenCV) library Version 2.4.11, with a PC equipped by Intel® Core i5 and 4G RAM, which processes one fluorescence microscopic image in less than 0.1 second.

The subject matter described herein could be implemented using a non-transitory, tangible processor-readable storage medium having stored thereon processor-readable instructions that, when executed by the processor of a programmable device, control the programmable device to perform a method according to embodiments of the present disclosure. Exemplary processor-readable storage media suitable for implementing the subject matter described herein include, but are not limited to, RAM, ROM, EPROM, EEPROM, flash memory or other solid-state memory technology, CD-ROM, DVD, or other optical storage, magnetic cassettes, magnetic tape, magnetic disk storage or other magnetic storage devices, and any other medium which can be used to store the desired information and which can be accessed by the processor. In addition, a processor-readable storage medium that implements the subject matter described herein may be located on a single device or computing platform or may be distributed across multiple devices or computing platforms.

In another aspect of the subject matter described herein, a system for identifying cells undergoing reprogramming and reprogrammed cells from a fluorescence microscopic image of one or more cells is provided. The system comprises an apparatus (hereinafter, a fluorescent image-capturing apparatus) configured to obtain a fluorescence microscopic image of one or more cells and a control unit. The fluorescent image-capturing apparatus is, for example, any suitable fluorescence microscope. The control unit is communicatively connected with the fluorescent image-capturing apparatus and is configured to process the fluorescence microscopic images captured by the apparatus. In particular, the control unit comprises a processor and a memory for storing a plurality of instructions which, when executed by the processor, causing the processor to perform the present method(s).

The communication between the fluorescent image-capturing apparatus and the control unit may be embodied using various techniques. For example, the system may comprise a network interface to permit communications between the fluorescent image-capturing apparatus and the control unit over a network (such as a local area network (LAN), a wide area network (WAN), the Internet, or a wireless network). In another example, the system may have a system bus that couples various system components including the fluorescent image-capturing apparatus to the control unit. In yet another embodiment, the system may have an output device for the fluorescent image-capturing apparatus to output the data representing the fluorescence microscopic image(s), and an input device for inputting these data into the control unit.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent.

Materials and Methods (1) IPS Cell Formation

Embryonic fibroblasts were derived from 13.5 d.p.c. embryos of a mouse line harboring doxycycline-inducible Oct4, Sox2, Klf4 and c-Myc. $1\times10^4$ embryonic fibroblasts were seeded in 3-cm dish in Dulbecco modified eagle's medium (DMEM) containing 10% fetal bovine serum (FBS) and incubated at 37° C. overnight. The medium was replaced with ES medium; GMEM containing 10% ES-certified FBS, 1% non-essential amino acid, 0.1% b-mercaptoethanol, 1000 μg/ml of LIF, 50 μg/ml of ascorbic acid, 3 μM CHIR99021. Two μg/ml of doxycycline were added to the medium to induce the transgene expression. The day of the doxycycline addition was assumed as day 0.

(2) Imaging Conditions

In this study, Leica Microsystem AF 6000LX (DFC360FX-442880310) was used to obtain live-cell time-lapse images. The microscope settings were summarized in Table 1, below. Two channels (Channel 1 & 2) of microscopy images were obtained simultaneously. The time-lapse fluorescence microscopy images were taken at an interval of 8 hours for 18 days.

TABLE 1

| Channel Name | Cube | Contrast Method | Intensity | Exposure Time | Peak Emission | Peak Excitation |
|---|---|---|---|---|---|---|
| Channel 1 | EMP | TL-PH | 100 | 0.990 ms | 0 nm | 1 nm |
| Channel 2 | L5 | FLUO | 5 | 400.0 ms | 520 nm | 499 nm |

Figure 2A:
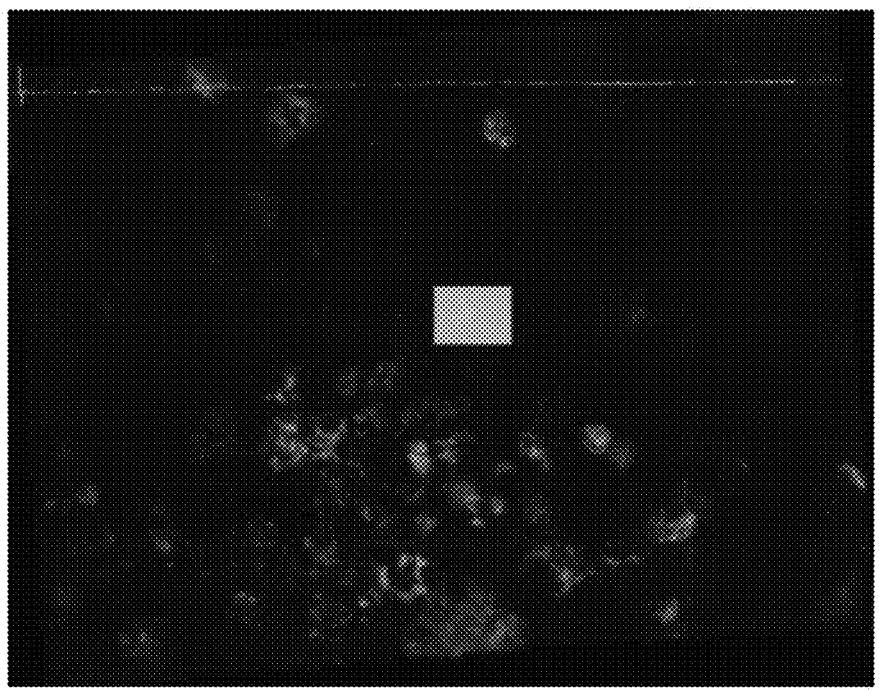
FIG. 2A is a fluorescence microscopic image of a mouse iPS cell culture according to one working example of the present disclosure.

FIG. 2A shows a large image consisted of 144 (12 by 12) fluorescence microscopic images. This image can reveal that the culturing field, wherein the highlighted microscopic image is shown in full resolution (1392×1020 pixels) as in FIG. 2B. The width of each pixel is 0.92 μm. An area with fluorescent cells can be observed in FIG. 2B.

Example 1

Figure 2B:
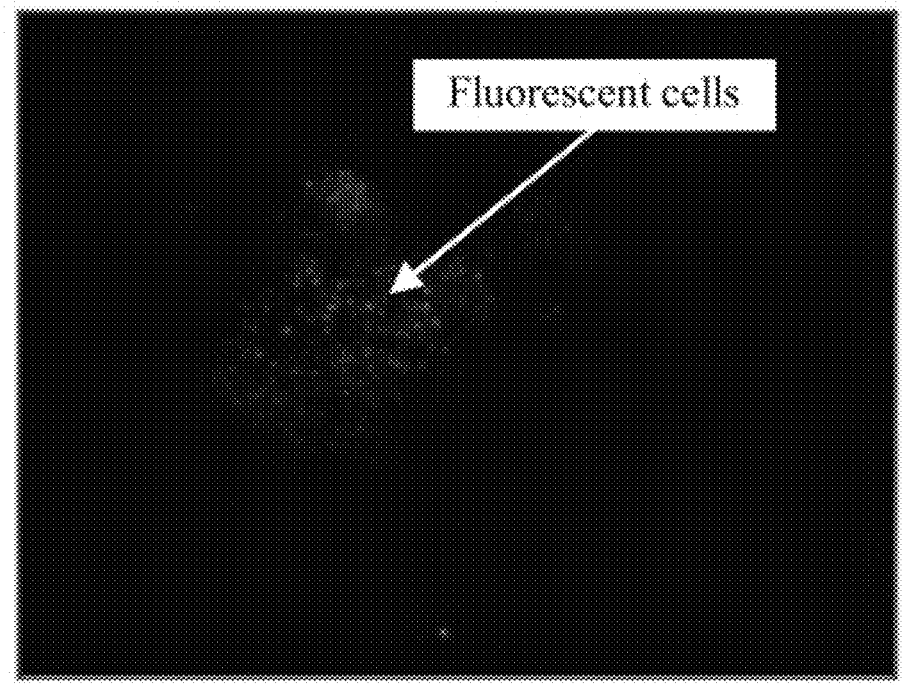
FIG. 2B is an enlarged view of the highlighted region in FIG. 2A.

In this example, the fluorescent image from FIG. 2B was processed by the imaging processing step S101 and the cell detection step S103, as described above, and the results were shown in FIG. 3, in which panel (a) is the original image; panel (b) shows the result after the image processing step S101 in which isolated fluorescent cells were well-enhanced because of unsharp masking; panel (c) shows the result after the cell detection step S103 in which a random color is assigned to a detected fluorescent cell or cell group; and panel (d) shows the image obtained by bright field contrast technique.

Figure 3:
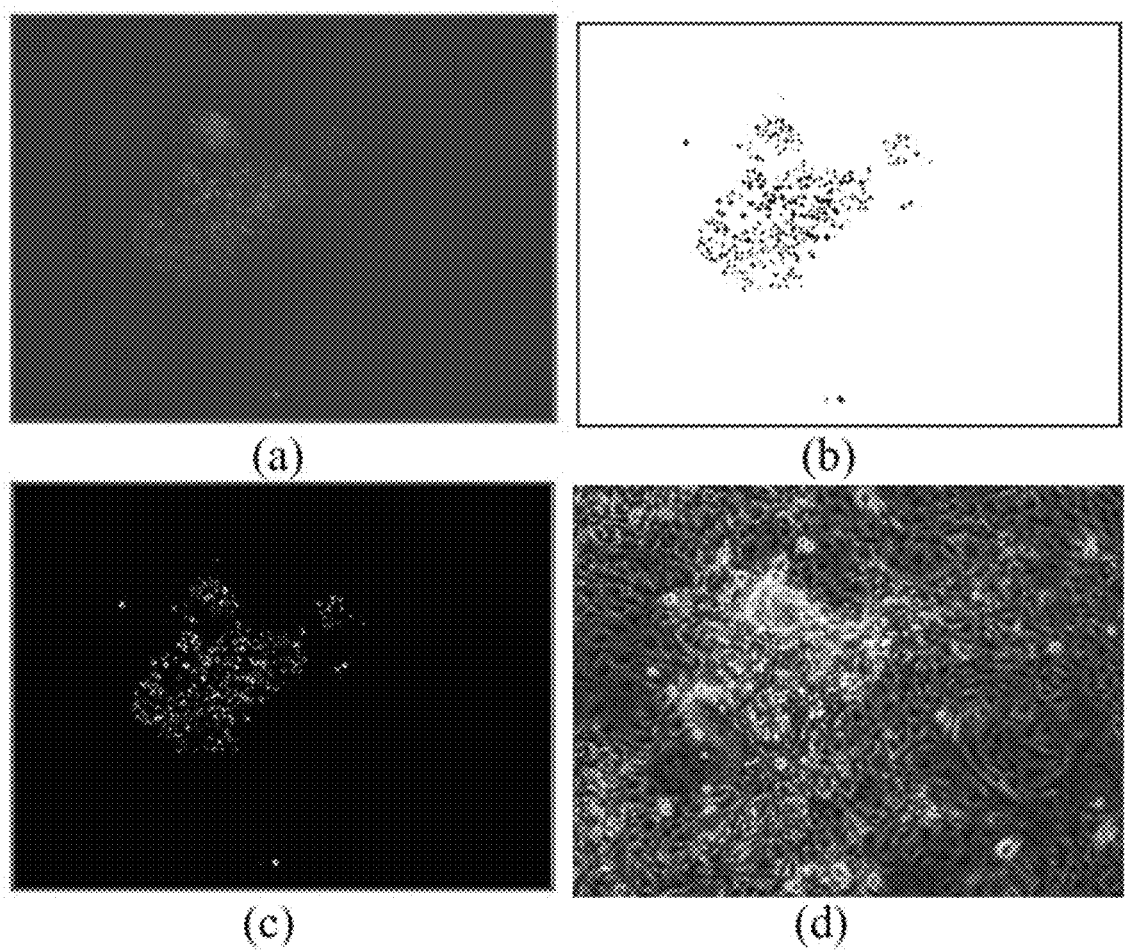
FIG. 3 shows an example of the implementation of the present method; panel (a), original fluorescent image; panel (b), image after the pre-processing step; panel (c), image after the cell detection step; and panel (d), original bright field contrast image.

A manual counting of fluorescent cells of panel (a) of FIG. 3 gave a result of 338 fluorescent cells. On the other hand, 334 fluorescent iPS cells are calculated in panel (c) of FIG. 3 using the present method. That is, an accuracy of about 98.5% was achieved using the present method.

Further, a comparison of panels (c) and (d) of FIG. 3 indicates that fluorescent cells identified by the present method (shown as the colored components in panel (c)) match the reprogrammed iPS cells and reprogramming iPS cells as shown in panel (d).

Example 2

In this example, two successive fluorescent images were processed by the imaging processing step S101, the cell detection step S103, and the cluster identification step S105, as described above, and the results were shown in FIG. 4, in which panels (a) and (b) show the original image and the corresponding bright field contrast image, respectively, and panels (c) and (d) show the result after the steps S101 to S103 of the image of panel (a) but with different standard deviations of gradients.

Figure 4:
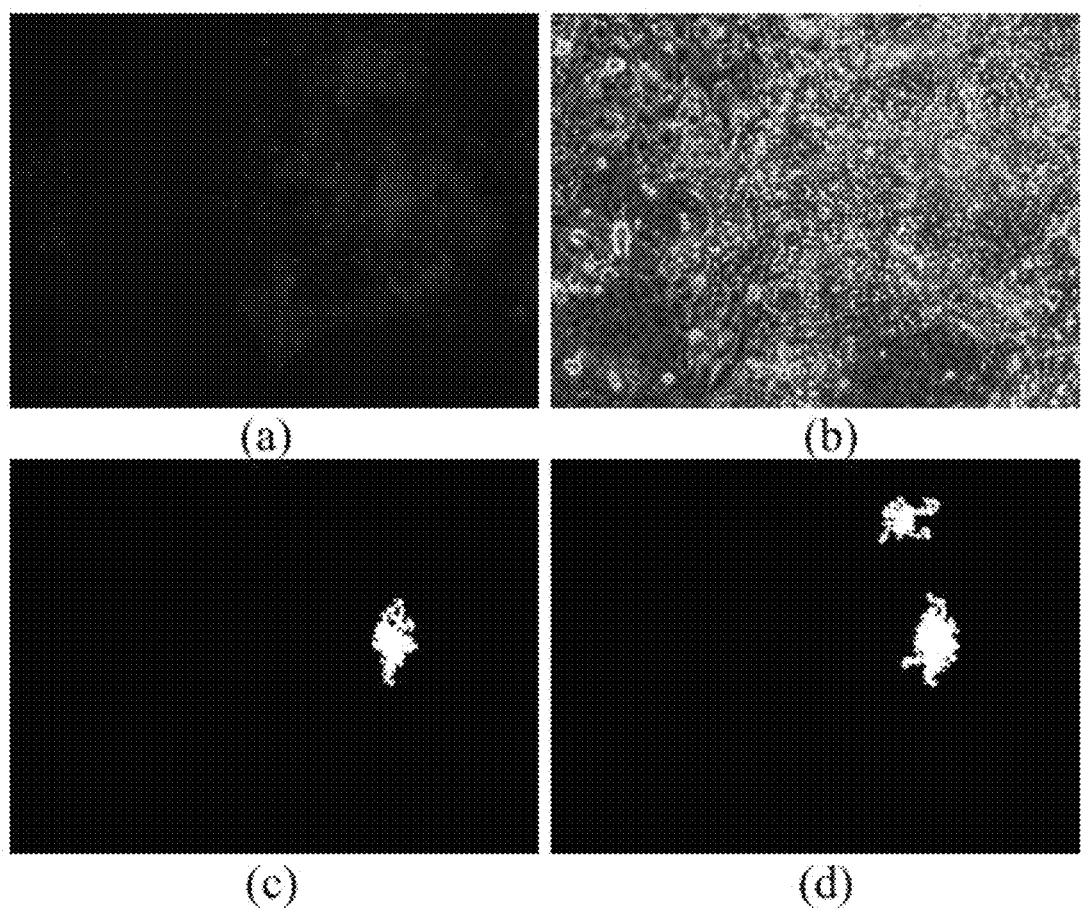
FIG. 4 shows an example of the implementation of the present method; panel (a), original fluorescent image; panel (b), original bright field contrast image; panels (c) and (d), images after the clustering step with different standard deviation of gradients.

As could be seen in panels (c) and (d) of FIG. 4, a vague (or smooth) region is found at the location(s) where the formation of iPS cells is taking place. The vagueness or smoothness is resulted from the stacking of the fluorescent cells during the reprogramming process. This result indicates the present method is capable of automatically identifying when and where the reprogramming process takes place from the fluorescence microscopic images.

These reprogrammed cell clusters can be further confirmed by cell biologists such as using the bright field contrast images thereof.

As is evident from the results of panels (c) and (d) of FIG. 4, adjusting the standard deviation of gradients in the cluster identification step S105 may give a different result. Accordingly, different standard deviations of gradients can be used in different imaging conditions, and a cell biologist can help choose an optimal one.

In view of the foregoing, the present method automatically analyzes time-lapse fluorescence microscopic images to characterize the mouse iPS cell formation process and therefore identifies when and where the reprogramming process might take place. This automated detection method can be used as on-line monitoring.

As could be appreciated, the size of the image presented in FIG. 2A is enormous, and a manual on-line detection for this image is considered impossible. However, using the present proper automated detection method in conjunction with advanced imaging devices (e.g., high-magnification, high-resolution, or 4D fluorescence microscope or camera), once the beginning of the reprogramming process is detected, the image capturing unit can be directed to (e.g., re-focused) to the location where the reprogramming takes place. In this way, the subsequent imaging range is limited to the locations where reprogramming and/or reprogrammed cells are, thereby providing a more efficient way for identifying reprogramming and/or reprogrammed cells.

The present methods, tangible computer-readable storage media, computer products, and/or systems are also applicable in quantitative analyses for analyzing and understanding the mechanism of the iPS formation and proliferation under different reagents or culture conditions. For example, the results from the cell detection step S103 can be analyzed to count the number of fluorescent cells and the iPS formation area over time, as well as their relations to the time, the position, and the speed about the iPS formation.

Moreover, the present method can analyze a large set of time-lapse fluorescence microscopic images in a short time, thereby reducing the tedious task performed by cell biologists conventionally. The present method exhibits a high accuracy that helps detect and locate the fluorescent cells in the microscopic images.

Furthermore, the cluster identification step S105 helps identify when and where the reprogramming process take place. Using the present method, images of the cells undergoing reprogramming and the reprogrammed cells can be captured to facilitate the understanding of the iPS formation process, as well as the relationship between this process and the cellular environment.

Embodiment 2

In this embodiment, an exemplary implementation of the system of Embodiment 1 is described.

Figure 5:
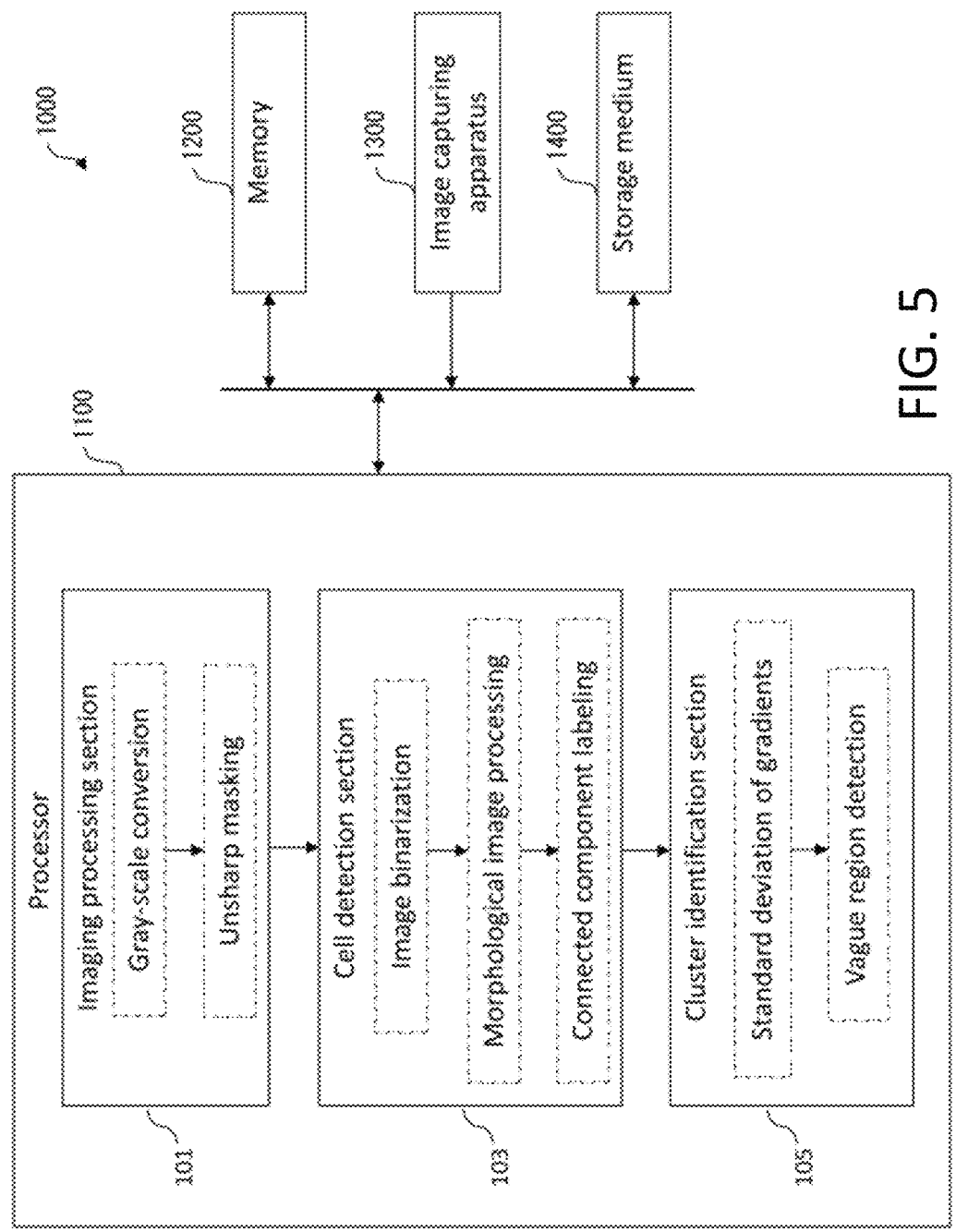
FIG. 5 is a block diagram illustrating a system for identifying cells undergoing reprogramming and reprogrammed cells according to Embodiment 2 of the present disclosure.

FIG. 5 shows a block diagram of the system for identifying cells undergoing reprogramming and reprogrammed cells from a fluorescence microscopic image of one or more cells which is explained in the first embodiment.

According to FIG. 5, the system 1000 comprises a processor 1100, a memory 1200, an image capturing apparatus 1300 and a storage medium 1400. As shown in FIG. 5, the processor 1100, the memory 1200, the image capturing apparatus 1300 and the storage medium 1400 are interconnected with one another via a system bus.

The image capturing apparatus 1300 corresponds to the fluorescent image-capturing apparatus of the first embodiment.

According to FIG. 5, the processor 1100 comprises an image processing section 101, a cell detection section 103 and a cluster identification section 105. The image processing section 101 performs the step S101 of the first embodiment. The cell detection section 103 performs the step S103 of the first embodiment. The cluster identification section 105 performs the step S105 of the first embodiment.

The memory 1200 stores a plurality of instructions which, when executed by the processor 1100, causing the processor to perform the method explained in the first embodiment.

The storage medium 1400 corresponds to the tangible computer-readable storage medium of the first embodiment. According to various embodiments of the present disclosure, the system 10000 comprises one or more devices (not shown) for accessing the instructions or codes stored in the tangible computer-readable storage medium 1400 and storing said instructions or codes in the memory 1200. Alternatively, the memory 1200 is or comprises the tangible computer-readable storage medium that is encoded with the computer-readable instructions according to the present disclosure.

As could be appreciated, it is also feasible to modify the present system 1000 so that it could be used to implement the methods described below in connection with Embodiments 3 and 4. For example, the storage medium 1400 and/or the memory 1200 may be used to store the instructions or codes for executing the method described above or equivalents thereof, and the processor is configured to perform said methods per the instructions or codes.

Embodiment 3

The third aspect of the present disclosure is directed to a method and an apparatus for iPS detection by deep learning. The present embodiment 3 comprises the method, system and apparatus which are already explained in the embodiments 1 and 2 as well as the method and apparatus explained below.

According to certain embodiments of the present disclosure, the method and the apparatus for iPS detection by deep learning of the present embodiment deal with the following 6 types of classes (Classification 1 to 6). The classes are defined by cell distribution and image texture (especially, Classification 4 to 6).

Figure 6:
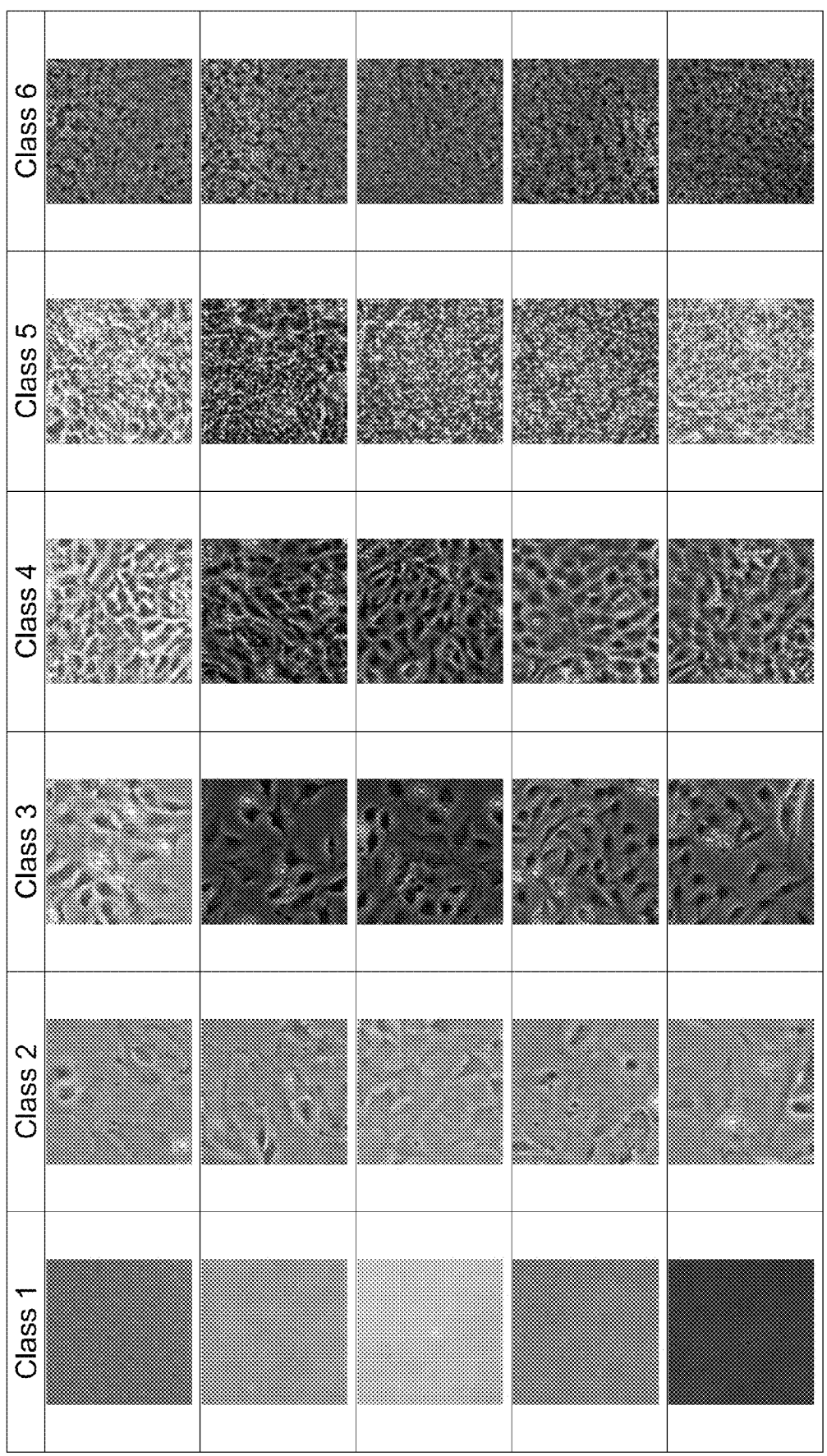
FIG. 6 shows exemplary images for each of the classification in the Embodiment 3.

Class 1: Region with no cells
Class 2: Region with separate cells
Class 3: Region with clustering cells
Class 4: Region with clustered cells
Class 5: Region with tightly clustered cells
Class 6: Region with iPS cells FIG. 6 shows representative images for each of the above class. Specifically, for class 1, there are no cells in the field of the image; that is, the field is completely empty. Regarding class 2, the cells are separated from each other, and there are gelatinous materials around cells. In class 3, cells are getting closer as the number of cells increases; in this stage, it is believed that the cells are undergoing reprogramming (iPS cells are showing). For class 4, cells in the field from a cell cluster with a rough pattern. In class 5, cells in the cluster get tighter and form a cluster with a meticulous pattern. As to class 6, the cells in the field are mostly iPS cells.

Figure 7:
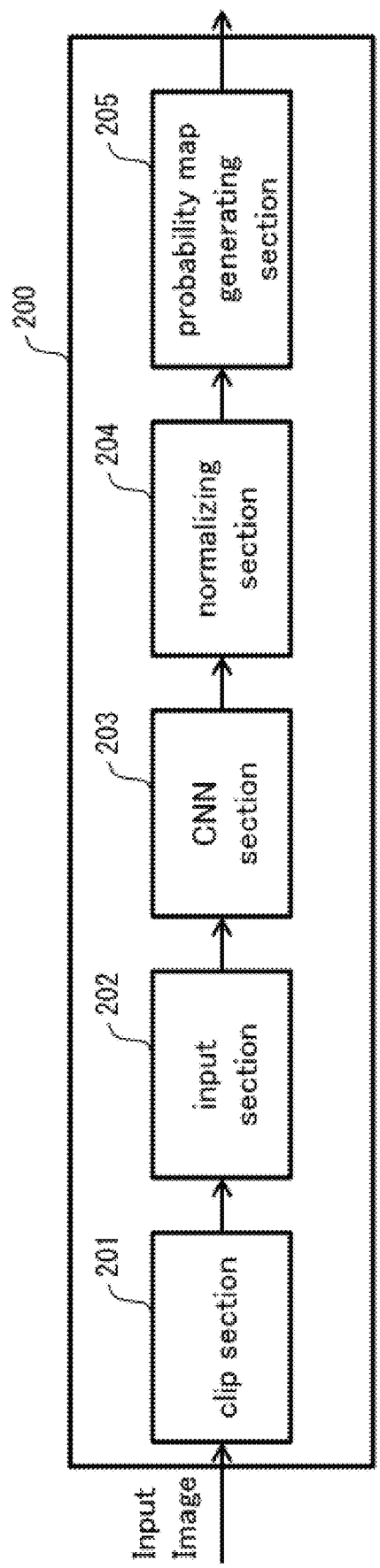
FIG. 7 is a block diagram of an iPS detection apparatus according to the Embodiment 3.
Figure 8:
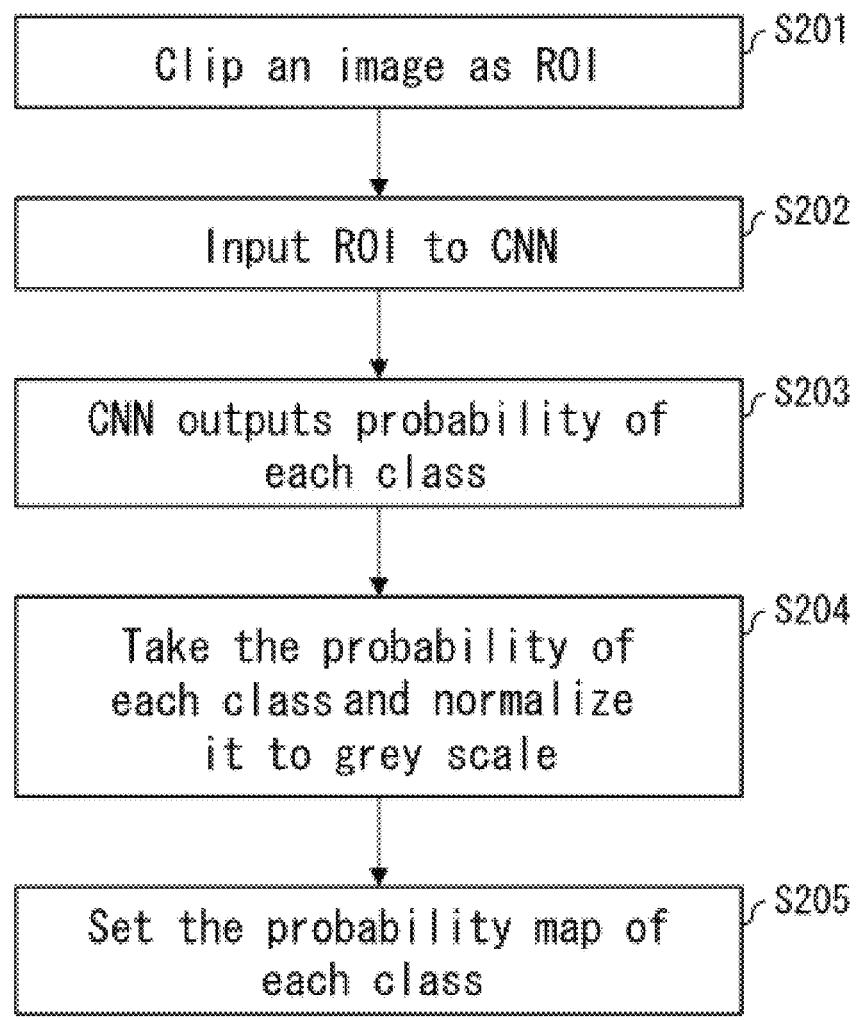
FIG. 8 is a flow diagram illustrating steps for performing the methods for detecting iPS on an image according to the Embodiment 3.

The apparatuses and methods for detecting identifying and tracing cells undergoing reprogramming and reprogrammed cells from a fluorescence microscopic image of one or more cells according to illustrative embodiments of the present disclosure is now discussed with reference to both FIG. 7 and FIG. 8. FIG. 7 is a block diagram of an iPS detection apparatus 200 according to the third embodiment of the present disclosure. FIG. 8 is a flow diagram illustrating steps for performing the method 200 for detecting iPS on an image, according to the present embodiment.

According to FIG. 7, the iPS detection apparatus 200 comprises a clip section 201, an input section 202, a convolutional neural network (CNN) section 203, a normalizing section 204 and a probability map generating section. The iPS detection apparatus 200 may be implemented in the system 1000 (in particular, in the processor 1100).

In operation, an input image is provided to the iPS detection apparatus 200. In step S201, upon receipt of the input image, the clip section 201 clips the input image as a region of interest (ROI). According to the embodiments of the present disclosure, the present method processes every pixel of the input image by using each pixel (x,y) as the center of the respective ROI. Note that although the pixel size of the ROI does not limit the present disclosure, an exemplary pixel size of the ROI is 256×256 pixels. Compared to the other sizes (e.g., 32×32, 64×64, 128×128), the size of 256×256 pixels works well especially with critical features of cell patterns. As could be appreciated, a pixel size greater than 256×256 is also applicable in the present invention.

In step S202, the ROI clipped by the clip section 201 is then provided to the input section 202, and the input section inputs the ROI to the CNN section 203.

Afterwards, in step S203, the CNN section 203 carries out a calculation based on a CNN deep learning framework on the ROI. The CNN section 203 outputs the probability of the ROI belonging to each classification, which is expressed as a fraction of 100 ranging from 0% to 100%.

The method then proceeds to step S204, in which the normalizing section 204 takes the probability of each class and normalizes it to a grey scale in the range of 0 255.

Then, in step S205, the probability map generating section 205 generates the probability map of each class. In this example, the normalized grey scale values of the six classes of each ROI are used to represent the probability map of the of the corresponding (x, y) pixel at the center of the ROI.

According to further embodiments of the present disclosure, the present method further comprises a step of visualization, in which the original fluorescence microscopic image is converted into a gray-level image using the probability map data of each pixel of the input image. Thereafter, the method may further comprise an analyzing step, in which a determination regarding the conditions of reprogramming and reprogrammed cells is made based on the gray-level image.

As could be appreciated, although in this embodiment, the normalization step S204 is performed before the step S205 regarding the generation of the probability map, it is also feasible to generate the probability map based on the probability results directly, and then convert (normalize) the probability map so that it is expressed with the grey scale value. In other words, after the step S203, the method proceeds first to step S205, followed by step S204. Still alternatively, it is also feasible to omit the step S204; that is, in such embodiments, the probability map is generated without normalization, and hence, the probability map may be expressed as a fraction of 100 ranging from 0% to 100%. In the case where no normalization step is performed, the probability map may be converted into a gray-level image using other known techniques. Alternatively, the data of the probability map may be used to determine the conditions of reprogramming and reprogrammed cells in the input image.

Also, it should be noted that according to certain embodiments, of the present embodiments, not every probability map of each class is normalized and/or converted into grey scale image. Rather, in some cases, only one or a selected number of classes is/are subjected to steps S204 and/or S205. For example, according to one embodiment, only the probability map of class 3 is normalized and visualized with a grey-scale image. In some other embodiments, only the probability map of class 5 is normalized and visualized with a grey-scale image.

Embodiment 4

According to preferred embodiments of the present disclosure, the CNN section 203 as illustrated in FIG. 7 comprises a trained CNN architecture. For example, the CNN architecture may be trained using a conventional deep learning frame work with or without modifications. In the present case, the CNN architecture is trained using convolutional architecture for fast feature embedding (Caffe) with some modifications. Briefly, this architecture includes 8 layers, in which 5 layers are used for convolution, ReLU, and poolingm whereas 3 layers are fully connected. Our modifications to the conventional Caffe architecture include: (1) image resolution is set as 256×256 pixels with no augmentation; (2) the processing order of pooling and the normalization is swapped; and (3) the results are 6 probabilities for the respective 6 classes.

Figure 9:
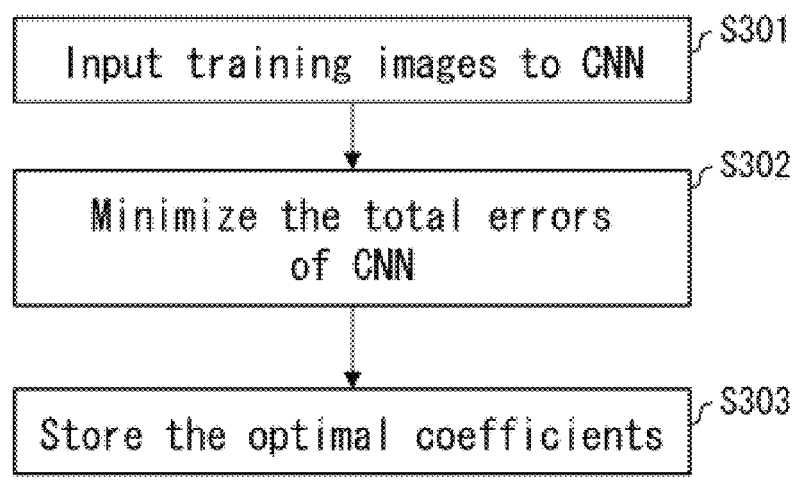
FIG. 9 is a flow diagram illustrating steps for performing the training process according to the Embodiment 4.

In this embodiment, the training process is implemented using the iPS detection apparatus 200 as illustrated in FIG. 7. FIG. 9 is a flow diagram illustrating steps for training the CNN architecture of the CNN section 203.

First, one or more training images are inputted to the clip section 201, which then clips a plurality of template images from each training image and deliver the template images to the input section 202. s Generally, the pixel size of the template image is the same as that of the region of interest (ROI) described above. For example, in preferred embodiments, the pixel size of the template image is 256 by 256.

Then, in the step S301, the input section 202 feeds the template image from the training image) to the CNN section 203.

In the step S302, the CNN section 203 optimizes the CNN classifier by iterating a plurality of template images to minimize the total errors of the deep learning model. Although the number of the template images does not restrict the present embodiment, in one exemplary training process, a total of 600 templates images (100 for each class) were extracted from 22 training images. In this case, 80 template images for each class are used for calculating the parameters of the CNN model and 20 for each class are used to calculate the error vectors of the parameters. The error vectors are then used to calculate the parameters again. The optimized parameters may be obtained after 10,000 iterations.

Next, in the step S303, the optimized parameters (that is, optimal coefficients) which have been derived in the step S302 are stored in a memory.

According to one aspect of the present embodiment, a template of the iPS class is used to obtain a feature (then used for coefficient optimization).

As could be appreciated, the CNN section 203, together with the optimal coefficients, forms a trained CNN architecture that may be used for further analysis. For example, the iPS detection apparatus 200 with the trained CNN architecture may be used to perform the process recited in FIG. 8. In this way, an image to be examined is fed to the iPS detection apparatus 200, the clip section 201 clips the image to as a region of interest (ROI), the CNN section 203 outputs the probability (0% 100%) of each class. For example, the iPS detection apparatus 200 classifies every pixel on the image as 6 probabilities of the 6 classes. Then, the probability map generating section 205 generates the probability map based on the probabilities derived in the CNN section 203. As an example, other than an imitation, the normalizing section 204 may take the probability of class 5 (iPS) and normalize it to grey scale (0~255); then, the probability map generating section 205 may generate the probability map of class 5 by giving the grey scale value to its corresponding (x, y) pixel.

Embodiment 5

In embodiment 5, images from different cell cultures were used to train the CNN architecture. Specifically, frozen human cord blood CD34 positive (CD34+) cells (from RIKEN BioResource Center, Tsukuba, Ibaraki, Japan) were thawed, washed with Stem Span SFEM (SFEM) medium (from StemCell Technologies, Vancouver, Canada) and resuspended in the expansion medium; SFEM supplemented with 20 ng/ml human stem cell factor (hSCF) and 50 ng/ml human thrombopoietin (hTPO). Cells were then seeded into a 24-well plate. After 24 hours of incubation, cells were collected and episomal vectors carrying reprogramming factor genes (pCXLE-hOCT3/4-shp53-F, pCXLE-hSK, and pCXLE-hUL, all from Addgene, Cambridge, Mass., USA) were introduced by electroporation using Amaxa Human CD34+ cell Nucleofector Kit and Nucleofector I devise (Lonza, Cologne, Germany). After 72 hours of incubation in the expansion medium, cells were collected, washed, resuspended in ES medium consisting of DMEM/HAM-F12 supplemented with 20% Knockout serum replacement, 1% non-essential amino acid, 2 mM L-glutamine, 0.1 mM 2-mercaproethanol, and 4 ng/ml human basic FGF and seeded into a matrigel (Corning)-coated 6-well plate. Then, small molecule inhibitor for Wnt secretion called IWP-2 was added to the medium at 2 µM when necessary (IWP-2 colony). The same volume of Dimethyl sulfoxide (DMSO) to dissolve IWP-2 was added to the medium as a control (DMSO colony). As a negative control, cells were also cultured without IWP-2 or DMSO (Control colony). At Day 5 of culture, floating cells and ES medium were completely removed and mTeSR1 (also from StemCell Technologies) was added to the culture. The culture medium was replaced every 2-3 days until human ES cell-like cells appeared.

All the images of cells undergoing reprogramming into iPS cells were taken by the light microscope (Olympus CKX41) equipped with digital color camera (Olympus DP25) and CellSens software. All the digital images are 24-bit color images with the image resolution of 2560 by 1920 pixels, and each image included only one colony. 24 sets of 6 time-lapse images were taken at Day 4, 7, 8, 9, 10 and 11, respectively. The 24 sets were named as Control colony 1~8, DMSO colony 1~8 and IWP-2 colony 1~8.

Among the 24 image sets, 132 images from 22 image sets were used as the training images to calculate the parameters of system models. Images from the remaining 2 image sets (IWP-2 colony 1 and Control colony 2; a total of 12 images) were used as test images to investigate the performance of the present system. Visual examination of the images by the laboratory staff revealed that there were four colonies have iPS cells, which are, control colony 1, days 10 and 11; DMSO colony 3, days 10 and 11; IWP-2 colony 1, days 10 and 11; and IWP-2 colony 6, days 10 and 11.

Figure 10:
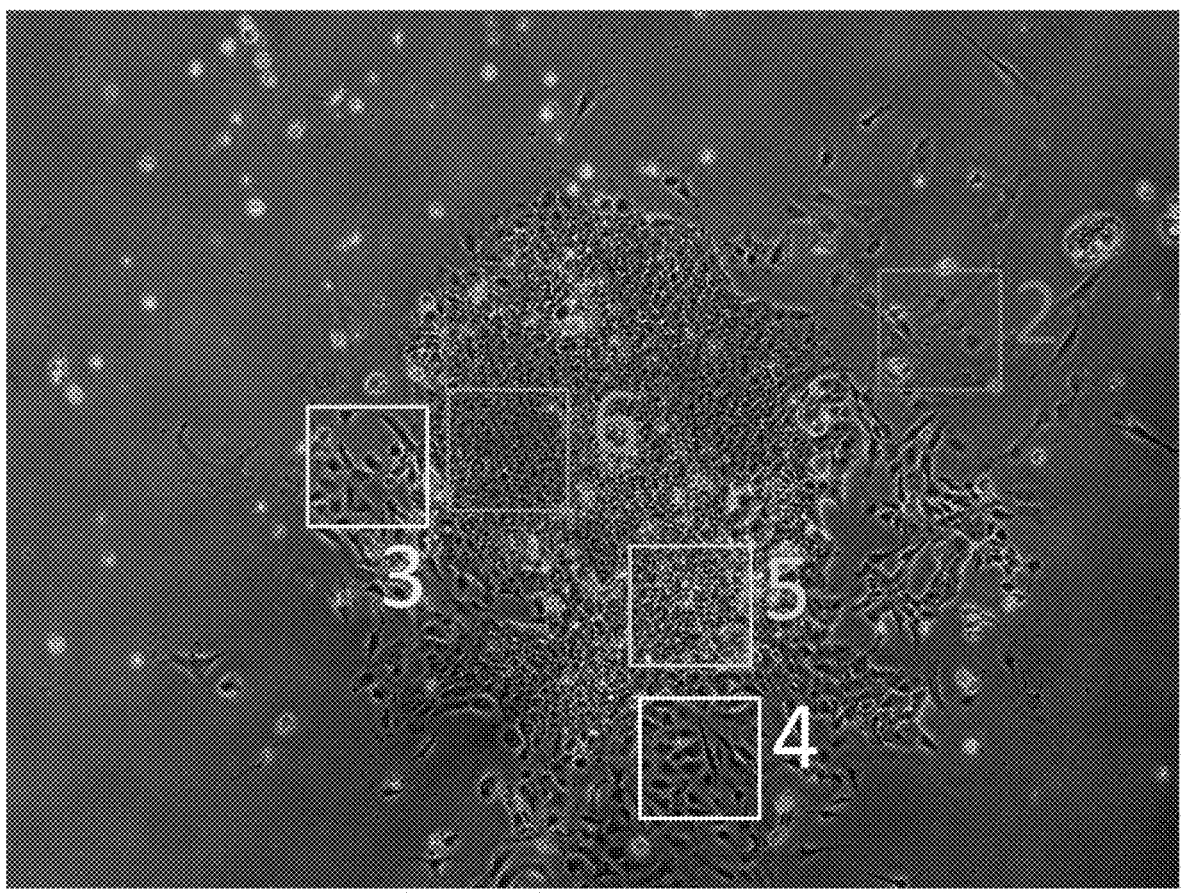
FIG. 10 shows one of the test images used in Embodiment 5.

In the training phase, the 22 image sets were processed as described in Embodiment 4 above. FIG. 10 is a representative image of a training image used in this embodiment. In FIG. 10, six illustrative template images were manually selected; these template images 1 to 6 respectively indicated cell patterns belonging to class 1 to 6, as defined in embodiment 2, above. Each of the template images as shown in FIG. 10, as well as template images from this and other training images, was then processed following the training method described in embodiment 4, above.

A total of 600 templates images (100 for each class) were extracted from the 132 training images, thereby establishing a CNN (Caffe) classifier in the CNN section 203. More specifically, as described above in embodiment 3, to train the CNN classifier in the CNN section 203, the input section provided a first portion of training images (80 images per class) to the CNN section 203; in this way, parameters for the CNN classifier were calculated. Furthermore, the input section 202 provided the remaining template images (20 templates per class) to the CNN section 203 to improve the parameters and to calculate error vectors in the CNN classifier. Again, the input section 202 provided 80 training images to the CNN section 203 in order to further improve the parameters and vectors in the CNN classifier.

Figure 11B:
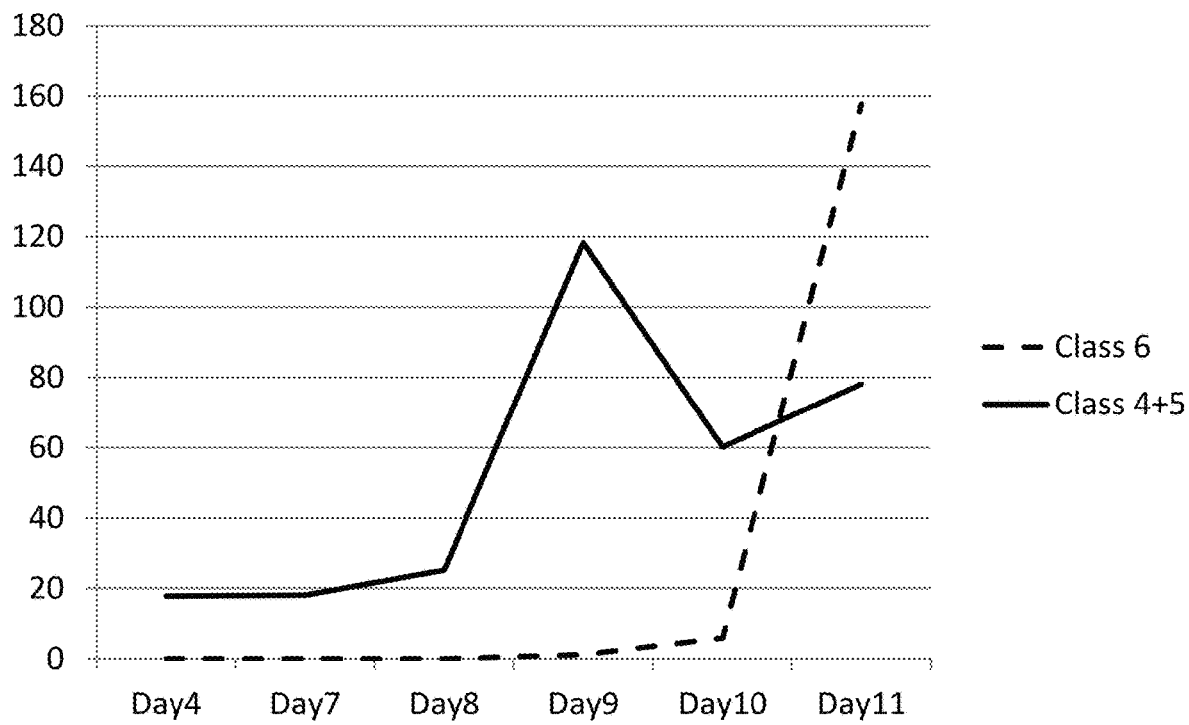
FIG. 11B and FIG. 11C are line graphs illustrating the detected intensity thereof.
Figure 11C:
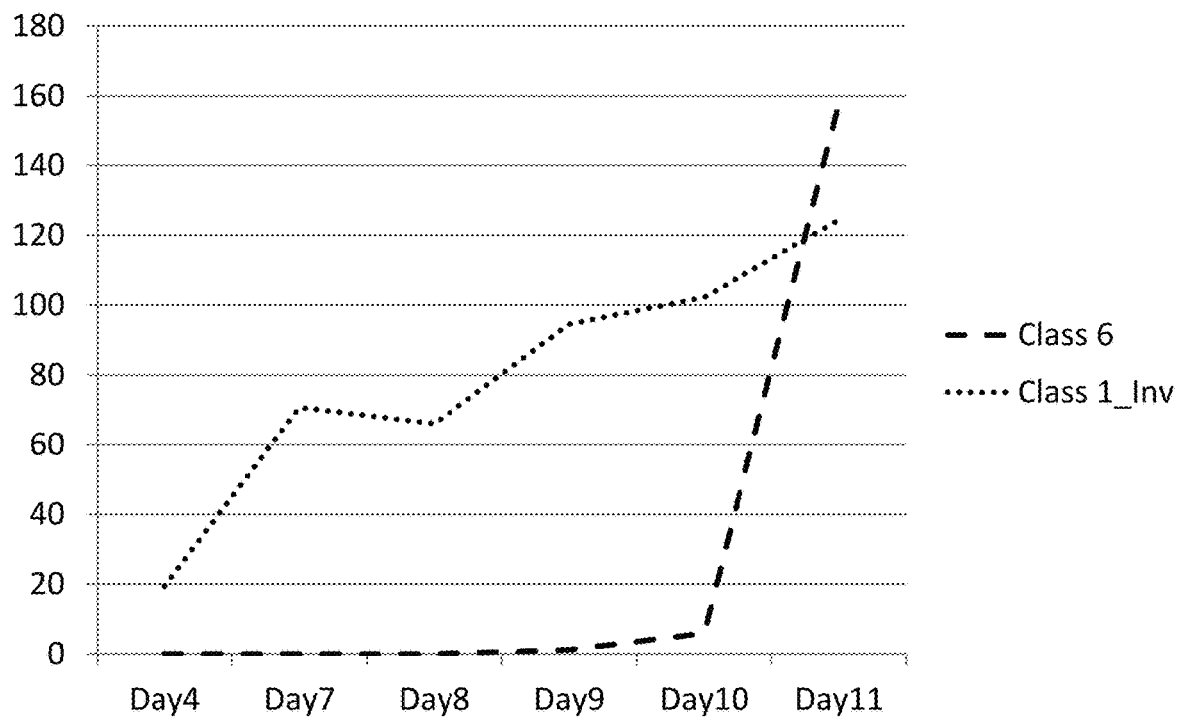
Figure 12B:
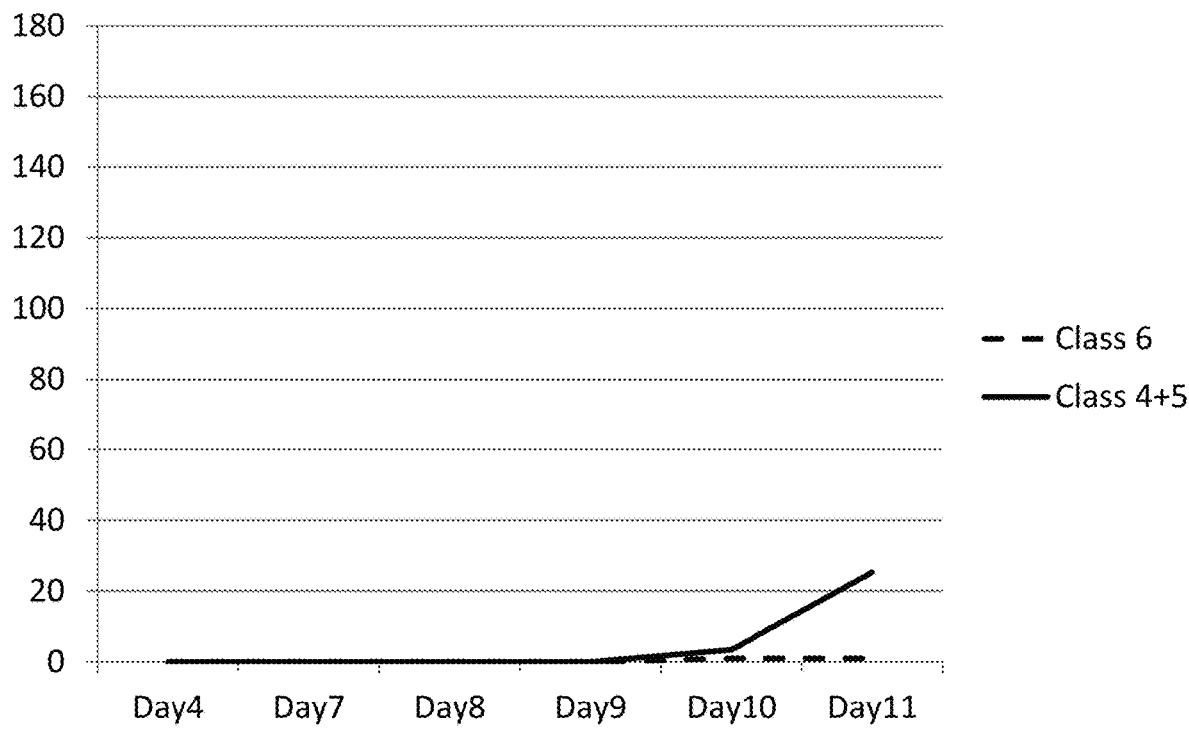
FIG. 12B and FIG. 12C are line graphs illustrating the detected intensity thereof.
Figure 12C:
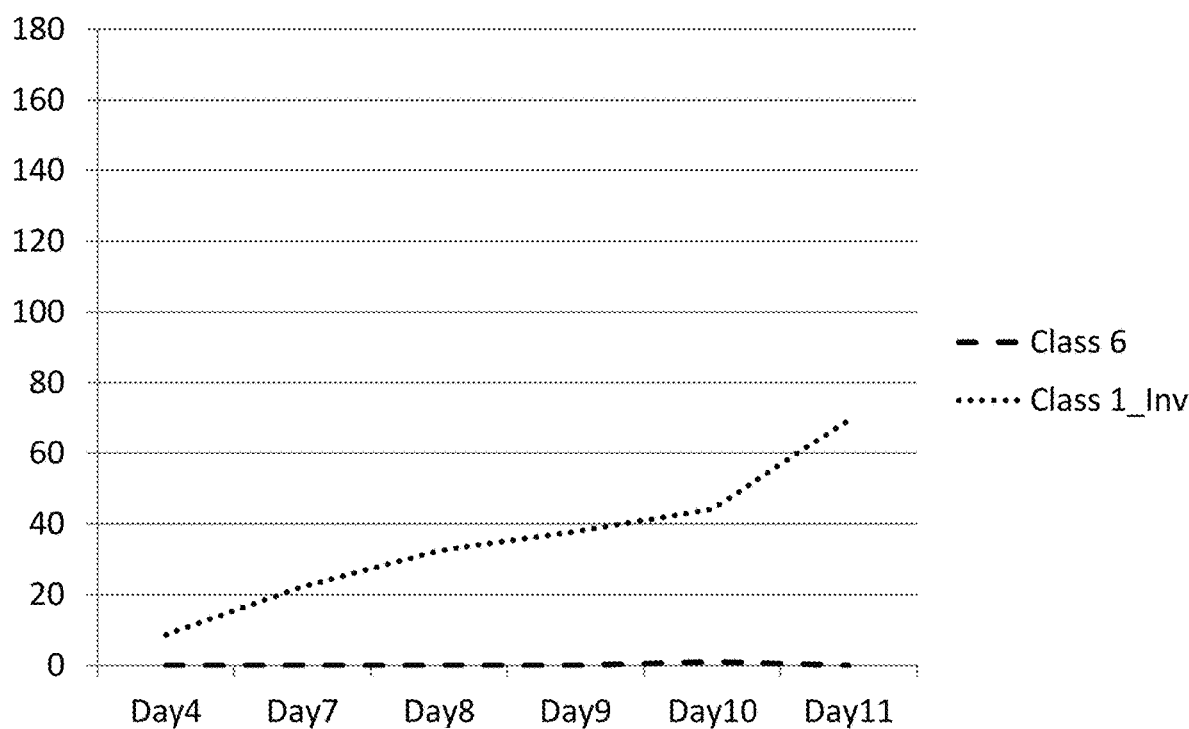

FIG. 11A and FIG. 12A respectively show exemplary images of IWP-2 colony 1 and Control colony 2, which were used as the training image in the present method. Specifically, FIG. 11A and FIG. 12A included original images taken at Day 4, 7, 8, 9, 10 and 11, as well as grey-scale images converted therefrom using class 4+5, class 6, and inversed class 1 probability maps. FIG. 11B and FIG. 12B are line graphs illustrating the intensity of detected cells of IWP-2 colony 6 and Control colony 2 in images using class 4+5 or class 6 probability maps in specified days. FIG. 11C and FIG. 12C are line graphs illustrating the intensity of detected cells of IWP-2 colony 6 and Control colony 2 in images using class 6 and inversed class 1 probability maps in specified days. It should be noted that the class 1 probability map contains mostly a blank area, and hence, the class 1 probability maps were inversed processed for the purpose of comparison and to facilitate the understanding of the present disclosure.

Referring to FIGS. 11A and 11B, reprogramming cells (class 4 and class 5 cells) started to from since Day 9 in the IWP-2 colony 1 culture, while reprogrammed cells (class 6 cells) were found around Day 11.

On the other hand, in FIG. 12A and FIG. 12B, no iPS cell were found in Control Colony 2 until the 11$^{th}$ day of culture; however, judging from the grey-scale images from reversed class 1, the cells grew slowly from Day 4 to Day 8. Also, the grey-scale images from class 4+5 indicated that the cells appeared to scatter in Day 11 (top and bottom panels of FIG. 12).

As could be seen in FIGS. 11A and 11B, the intensity observed in the class 6 probability maps was correlated with the intensity observed in the class 4-5 probability maps. Similar results were seen in FIGS. 12A and 12B.

Also, by comparing FIG. 11A and FIG. 12A, it is found that the significant increase of the average intensity of the class 4 and class 5 probability maps during Day 4 to Day 7 indicated that the cells in this colony grew rapidly and tended to aggregate; as compared with other colonies where no significant increase of the average intensity of the class 4 and class 5 probability maps was found during the same period, it was more likely to seen iPS cells in the former colony in Day 10 to Day 11.

On the other hand, during Day 4 to Day 7, if the average intensity of the class 1 probability map of a colony decreased rapidly, meaning that during said period, cells in that colony grew and scattered rapidly. By comparing FIG. 11A, FIG. 12A, FIG. 11C and FIG. 12C, it is found that as compared with other colony that did not exhibit a significant decrease in the class 1 probability maps, the colony that did show significant decrease was more likely to form iPS cells in Day 10 and Day 11.

It should be appreciated by persons having ordinary skill in the art, the more training images the higher the accuracy of the present method. In this embodiment, the images in FIG. 11 and images from other training images were subjected to 10,000 iterations during the present training process.

In this embodiment, the training process was implemented using a personal computer equipped with Intel Core i5-6400 2.7 GHz, 8 GB Ram, and NVIDIA GeForce GTX 950 (with CUDA 7.5). The software was developed using C/C++ programming and the OpenCV library.

In this way, type I (false positive) error and type II (false negative) error rates of 9.2% and 0.84% were achieved. The average execution time for classifying a template was approximately 0.076 seconds. Table 2 shows the classification results for the 120 templates. For examples, 19 templates of Class 6 templates were correctly classified, and only one was classified as Class 5. The results demonstrated that the present system may achieve a satisfactory classification accuracy.

TABLE 2

| Manual | CNN Classification | | | | | |
|---|---|---|---|---|---|---|
| Classification | Class 1 | Class 2 | Class 3 | Class 4 | Class 5 | Class 6 |
| Class 1 | 1 | 0 | 0 | 0 | 0 | 0 |
| Class 2 | 0.15 | 0.85 | 0 | 0 | 0 | 0 |
| Class 3 | 0 | 0.25 | 0.75 | 0 | 0 | 0 |
| Class 4 | 0 | 0 | 0.1 | 0.9 | 0 | 0 |
| Class 5 | 0 | 0 | 0 | 0 | 1 | 0 |
| Class 6 | 0 | 0 | 0 | 0 | 0.05 | 0.95 |

Then, the CNN section 203 was used to classify the test image into any of the 6 classes. The area changes of 6 classes during a set of time-series (6) images shows the relation of growths between iPS cells and other types of cells.

Specifically, after the training process, the test images, i.e., images from image sets of IWP-2 colony 1 (FIG. 11A) and Control colony 2 (FIG. 12A), were fed into the iPS detection apparatus 200 with the trained CNN architecture stored therein.

In the present embodiment, approximately 103 minutes were used to create the 6 gray-level probability images for each test image.

Figure 13:
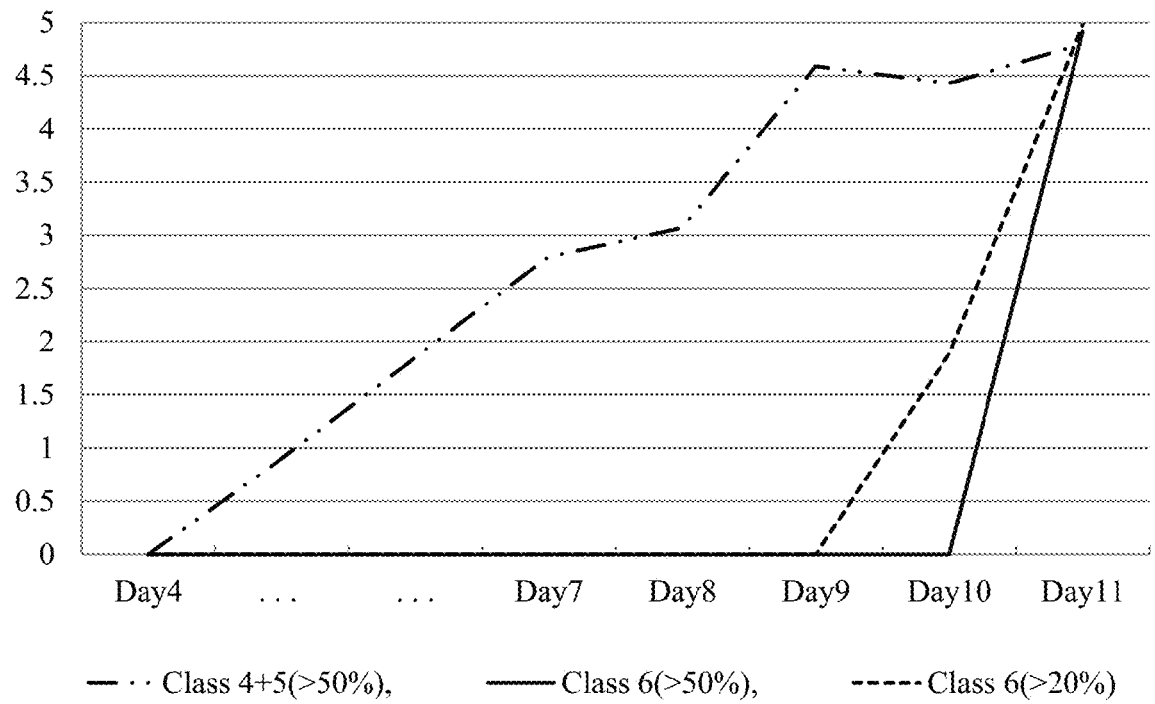
FIG. 13 is a line graph illustrating the number of pixels over 50% probability classified as Class 4+5, 50% probability classified as Class 6 and 20% probability classified as Class 6 of Embodiment 5, in which the log value of the pixel number is plotted against the culturing time.

The growth condition of the cell was also determined using the probability maps by summing up the number of pixels belonging to each class. FIG. 13 is a line graph summarizing the growth condition of the IWP-2 colony 1. In particular, the graph indicates the log value of pixels being classified as: having at least a 50% probability of belonging to class 4 or 5, having at least a 50% probability of belonging to class. Or having at least a 20% probability of belonging to class. As indicated above, cells with patterns of class 4 and 5 are considered reprogramming iPS cells, while cells with patterns of class 6 are considered reprogrammed iPS cells. As could be seen in FIG. 13, the reprogrammed human iPS cells increased rapidly after the occurrence of a certain number of reprogramming iPS cells.

Figure 14:
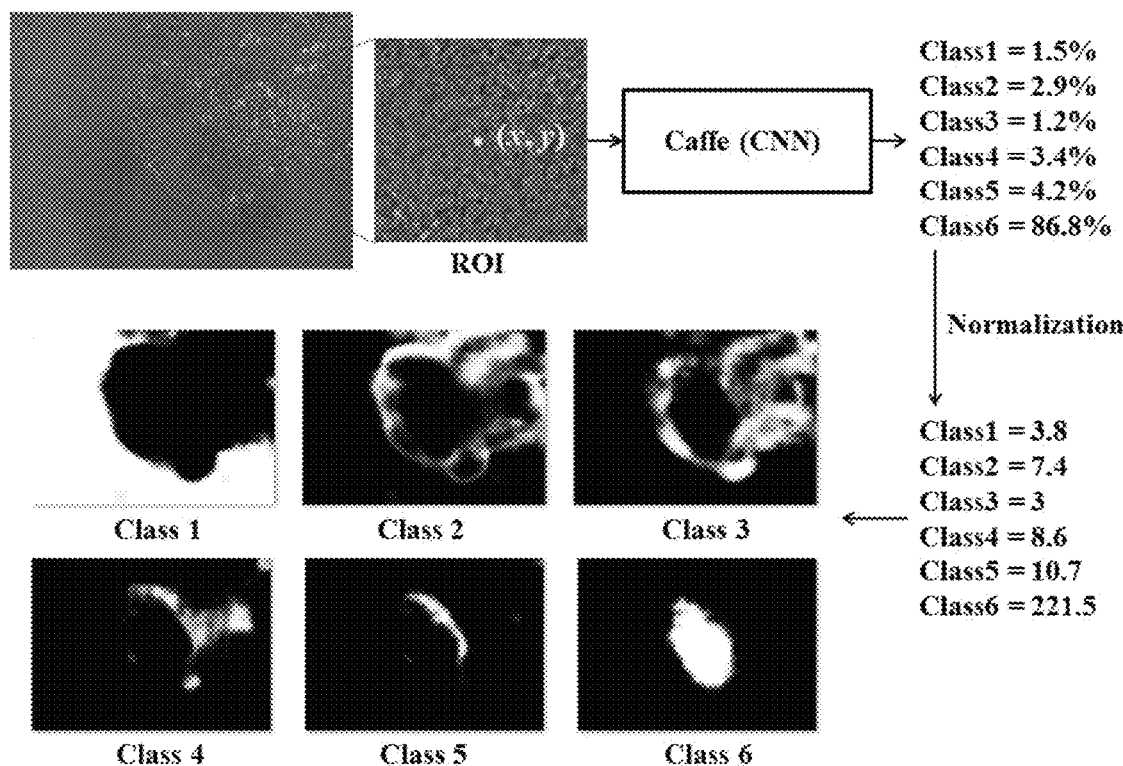
FIG. 14 shows a representative process of the CNN classification, generation of probabilities of the six classes, normalization of probabilities, and visualization of the probability maps according to Embodiment 5.

FIG. 14 shows the exemplary processing steps of the ROI the image taken on Day 11 of the IWP-2 colony 1 culture. In particular, the pixel (x,y) was the center of the ROI, and the Caffe architecture of the CNN outputted the probabilities of the pixel (x, y) belonging to each of the classes, which were then normalized to express the grey-scale level of the pixel (x, y), and then grey-scale images were generated from the probability maps of each group.

According to the present embodiment, a 94% accuracy was achieved for the test images using the trained Caffe architecture.

Note that the training step and test step may be performed iteratively. In the iteration, test images which have been once used in the test step may also be used as input images in the training step. Also, the test result may be fed back to the training step and improve the parameters and vectors in the CNN classifier. By iterating these procedures, the further optimization of the CNN classifier is achieved.

Embodiment 6

This embodiment provides more detailed explanations about training images and test images. One aspect of the present embodiment comprises a variation of the third and fourth embodiments. Another aspect of the present embodiment comprises a supplement to the third and fourth embodiments.

According to the present embodiment, the training images and test images may be taken as follows.

(Case 1): the training image is a fluorescence image, and the test image is a non-fluorescence image.

(Case 2): the training image is a non-fluorescence image, and the test image is a non-fluorescence image.

(Case 3): the training image is a fluorescence image, and the test image is a fluorescence image.

(Case 4): the training image is a non-fluorescence image, and the test image is a fluorescence image.

According to the present embodiment, in any of the above cases, the test result may be fed back to the training step.

For example, in the above case 1 and 2, the training step may be performed based on the fluorescence images or non-fluorescence images. Then, the test step is performed based on the non-fluorescence test images. Here, the test result based on the non-fluorescence test image may be fed back to the training step which deals with non-fluorescence training images. This procedure may be preferable in the sense that we do not need to provide fluorescence materials into the target cells in the second training step. Also, this procedure may be preferable because training step with non-fluorescence training images may be cost efficient. Further, this procedure may be preferable in the sense that we may have higher throughput when the detection is carried out based on the non-fluorescence images.

As another example in the above case 1 and 2, the training step may be performed based on the fluorescence images or non-fluorescence images. Then, the test step is performed based on the non-fluorescence test images. Here, the test result based on the non-fluorescence test image may be fed back to the training step which deals with fluorescence training image. This procedure may be preferable in the sense that we may have higher throughput when the detection is carried out based on the non-fluorescence images. Therefore, it is preferable that the training step is carried out based on the non-fluorescence images and use fluorescence images as test images in the test step.

As for the above case 3 and 4, for example, the training step may be performed based on the fluorescence images or non-fluorescence images. Then, the test step is performed based on the fluorescence test images. Here, the test result based on the fluorescence test image may be fed back to the training step which deals with non-fluorescence training images. This procedure may be preferable in the sense that we do not need to provide fluorescence materials into the target cells in the second training step. Also, this procedure may be preferable because training step with non-fluorescence training images may be cost efficient.

As another example in the above case 3 and 4, the training step may be performed based on the fluorescence images or non-fluorescence images. Then, the test step is performed based on the fluorescence test images. Here, the test result based on the fluorescence test image may be fed back to the training step which deals with fluorescence training image. This procedure may be preferable because training and test step with fluorescence images may increase the detecting precision.

As shown in the above cases 1 to 4, the training step may be carried out with fluorescence images or non-fluorescence images. This aspect may be preferable because it increases the freedom of how to perform the training step. Also, as shown in the above cases 1 to 4, the test step may also be carried out with fluorescence images or non-fluorescence images. This aspect may be preferable because it increases the freedom of how to perform the test step.

It will be understood that the above description of embodiments is given by way of example only and that various modifications and combinations may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for identifying cells undergoing reprogramming and reprogrammed cells from a fluorescence microscopic image of one or more cells, comprising the steps of,
    (a) applying grayscale conversion and unsharp masking to the fluorescence microscopic image to obtain an enhanced image;
    (b) converting the enhanced image to a binary image;
    (c) identifying a cell-like ellipse boundary for cells in the binary image, wherein each cell-like ellipse boundary represents an isolated cell or a group of cells; and
    (d) labeling each isolated cell or group of cells with a random color to obtain a plurality of colored components, wherein each color component represents one or more cells undergoing reprogramming or one or more reprogrammed cells;
    wherein in the step (a), the unsharp masking is performed by applying an unsharp mask according to equation 1:

$$f_s(x,y) = |f(x,y) - f(x,y) * G_\sigma| \quad \text{(equation 1)},$$

where the fs(x,y) is the enhanced image, x and y are the image coordinates, * represents the image convolution, and Gσ is the Gaussian filter with the standard deviation σ and the filter size of 2σ+1.

2. The method of claim 1, wherein the step (b) is performed according to equation 2:

$$g(x, y) = \begin{cases} 1 & f_s(x, y) \geq T \\ 0 & \text{otherwise} \end{cases}, \quad \text{(equation 2)}$$

where T is the threshold for the fluorescence microscopy image.

3. The method of claim 1, further comprising the steps of,
    (e) evaluating the smoothness of each pixel of the colored components in relative to a local area of the pixel by,
    (e-1) determining the magnitude of image gradients M(x, y) of each pixel according to equation 3:

$$M(x,y) = \sqrt{G_x^2 + G_y^2}, \quad \text{(equation 3)},$$

where $G_x = \partial f/\partial x$ and $G_y = \partial f/\partial y$, Gx and Gy respectively represent the image gradients in x and y directions, and
    (e-2) determining the smoothness σ(x,y) of each pixel according to equation 4:

$$\sigma(x, y) = \frac{1}{N-1} \sum_x \sum_y (M(x, y) - \mu)^2, \quad \text{(equation 4)}$$

where N is the total number of pixels and μ is the mean pixel value in the local area; and
    (f) determining the presence of a vague region R that satisfies the criterion of equation 5:

$$R = \{(x,y): \sigma(x,y) \geq T\} \quad \text{(equation 5)}.$$

4. The method of claim 3, wherein the method comprises performing steps (a) to (f) to a series of fluorescence microscopic images of said one or more cells to identify the beginning of the cell reprogramming.

5. A non-transitory, tangible computer-readable storage medium, encoded with computer-readable instructions for executing a method of claim 1.

6. The non-transitory, tangible computer-readable storage medium of claim 5, wherein the step (b) is performed according to equation 2:

$$g(x, y) = \begin{cases} 1 & f_s(x, y) \geq T \\ 0 & \text{otherwise} \end{cases}, \qquad \text{(equation 2)}$$

where T is the threshold for the fluorescence microscopy image.

7. The non-transitory, tangible computer-readable storage medium of claim 5, wherein the method further comprises the steps of,
   (e) evaluating the smoothness of each pixel of the colored components in relative to a local area of the pixel by,
   (e-1) determining the magnitude of image gradients M(x, y) of each pixel according to equation 3:

$$M(x,y) = \sqrt{G_x^2 + G_y^2} \bullet \qquad \text{(equation 3)},$$

where $G_x = \partial f/\partial x$ and $G_y = \partial f/\partial y$, Gx and Gy respectively represent the image gradients in x and y directions, and
   (e-2) determining the smoothness σ(x,y) of each pixel according to equation 4:

$$\sigma(x, y) = \frac{1}{N-1} \sum_x \sum_y (M(x, y) - \mu)^2, \qquad \text{(equation 4)}$$

where N is the total number of pixels and μ is the mean pixel value in the local area; and
   (f) determining the presence of a vague region R that satisfies the criterion of equation 5:

$$R = \{(x,y) : \sigma(x,y) \geq T\} \qquad \text{(equation 5)}.$$

8. A system for identifying cells undergoing reprogramming and reprogrammed cells from a fluorescence microscopic image of one or more cells, comprising,
   an apparatus configured to obtain a fluorescence microscopic image of one or more cells; and
   a control unit, comprising a processor and a memory for storing a plurality of instructions which, when executed by the processor, causing the processor to perform a method of claim 1.

9. The system of claim 8, wherein the step (b) is performed according to equation 2:

$$g(x, y) = \begin{cases} 1 & f_s(x, y) \geq T \\ 0 & \text{otherwise} \end{cases}, \qquad \text{(equation 2)}$$

where T is the threshold for the fluorescence microscopy image.

10. The system of claim 8, wherein the method further comprises the steps of,
   (e) evaluating the smoothness of each pixel of the colored components in relative to a local area of the pixel by,
   (e-1) determining the magnitude of image gradients M(x, y) of each pixel according to equation 3:

$$M(x,y) = \sqrt{G_x^2 + G_y^2} \bullet \qquad \text{(equation 3)},$$

where $G_x = \partial f/\partial x$ and $G_y = \partial f/\partial y$, Gx and Gy respectively represent the image gradients in x and y directions, and
   (e-2) determining the smoothness σ(x,y) of each pixel according to equation 4:

$$\sigma(x, y) = \frac{1}{N-1} \sum_x \sum_y (M(x, y) - \mu)^2, \qquad \text{(equation 4)}$$

where N is the total number of pixels and μ is the mean pixel value in the local area; and
   (f) determining the presence of a vague region R that satisfies the criterion of equation 5:

$$R = \{(x,y) : \sigma(x,y) \geq T\} \qquad \text{(equation 5)}.$$

11. A method for identifying and tracing cells undergoing reprogramming and reprogrammed cells from a fluorescence microscopic image of one or more cells, comprising the steps of,
   (a) for every pixel of the fluorescence microscopic image, capturing an image of region of interest (ROI) of the pixel;
   (b) applying a trained convolutional neural network (CNN) model to the ROI to calculate the respective probabilities of the pixel belonging to any of a plurality of classes, wherein each of the plurality classes indicate a cell clustering pattern of the ROI; and
   (c) obtaining a plurality of probability maps that respectively indicate the probabilities of the plurality of classes at every pixel of the fluorescence microscopic image;
   wherein in the step (b), the trained CNN model is established by a training method comprising the steps of,
   (1) selecting a region of a training image as a template image;
   (2) manually classifying the template image as belonging to one of the plurality of classes;
   (3) producing a training set comprising a plurality of template images from a plurality of training images by repeating steps (1) and (2); and
   (4) using the plurality of template images of the training set as inputs to train an CNN architecture to obtain the trained CNN model;
   wherein in the step (3), the plurality of template images are divided into a first set of template images and a second set of template images, and in the step (4), the method comprising the steps of,
   using the first set of template images to calculate a plurality of parameters of the CNN model;
   using the second set of template images to calculate a plurality of error vectors of the plurality of parameters; and
   using the error vectors to re-calculate the parameters.

12. The method of claim 11, further comprising the step of,
   (d) converting the fluorescence microscopic image into a gray-level image according to the plurality of probability maps.

13. The method of claim 12, further comprising the step of,
   (e) determining the conditions of reprogramming gray-level image.

14. The method of claim 11, wherein the pixel size of the ROI is at least 256 by 256 pixels.

15. A non-transitory, tangible computer-readable storage medium, encoded with computer-readable instructions for executing a method of claim 11.

16. A system for identifying and tracing cells undergoing reprogramming and reprogrammed cells from a fluorescence microscopic image of one or more cells, comprising,
- an apparatus configured to obtain a fluorescence microscopic image of one or more cells; and
- a control unit, comprising a processor and a memory for storing a plurality of instructions which, when executed by the processor, causing the processor to perform a method of claim 11.

* * * * *